US008679735B2

(12) United States Patent
Fahy et al.

(10) Patent No.: US 8,679,735 B2
(45) Date of Patent: Mar. 25, 2014

(54) METHODS AND COMPOSITIONS FOR THE CRYOPRESERVATION OF ORGANS

(75) Inventors: Gregory M. Fahy, Corona, CA (US); Brian Wowk, Corona, CA (US)

(73) Assignee: 21st Century Medicine Inc., Rancho Cucamonga, CA (US)

( * ) Notice: Subject to any disclaimer, the term of this patent is extended or adjusted under 35 U.S.C. 154(b) by 1468 days.

(21) Appl. No.: 10/571,968

(22) PCT Filed: Sep. 16, 2004

(86) PCT No.: PCT/US2004/030544
§ 371 (c)(1),
(2), (4) Date: Nov. 8, 2006

(87) PCT Pub. No.: WO2005/027633
PCT Pub. Date: Mar. 31, 2005

(65) Prior Publication Data
US 2007/0190517 A1 Aug. 16, 2007

Related U.S. Application Data

(60) Provisional application No. 60/503,551, filed on Sep. 16, 2003.

(51) Int. Cl.
*A01N 1/00* (2006.01)

(52) U.S. Cl.
USPC .............................. 435/1.2; 435/1.3; 435/1.1

(58) Field of Classification Search
None
See application file for complete search history.

(56) References Cited

U.S. PATENT DOCUMENTS

| | | | |
|---|---|---|---|
| 5,723,282 A | 3/1998 | Fahy et al. | |
| 5,821,045 A | 10/1998 | Fahy et al. | |
| 5,962,214 A | 10/1999 | Fahy et al. | |
| 6,187,529 B1 | 2/2001 | Fahy et al. | |
| 6,274,303 B1 * | 8/2001 | Wowk et al. | 435/1.3 |
| 6,395,467 B1 | 5/2002 | Fahy et al. | |
| 2002/0042042 A1 * | 4/2002 | Fahy | 435/1.3 |

FOREIGN PATENT DOCUMENTS

| | | |
|---|---|---|
| WO | WO 96/05727 | 2/1996 |
| WO | WO 01/42388 | 6/2001 |
| WO | WO 02/09516 | 6/2001 |
| WO | WO 03/009743 | 2/2003 |
| WO | WO 03/065801 | 8/2003 |

OTHER PUBLICATIONS

Arnaud, et al., *Physiological evaluation of a rabbit kidney perfused with VS41A*. Cryobiology, 2003. 46: 289-294.
Fahy, G.M., *Analysis of "solution effects" injury: cooling rate dependence of the functional and morphological sequellae of freezing in rabbit renal cortex protected with dimethyl sulfoxide*. Cryobiology, 1981. 18: 550-570.
Fahy, G.M., *Prospects for vitrification of whole organs*. Cryobiology, 1981. 18: 617.
Fahy, G.M., *Cryoprotectant toxicity: biochemical or osmotic?* Cryo-Letters, 1984. 5: 79-90.
Fahy, et al., *Some emerging principles underlying the physical properties, biological actions, and utility of vitrification solutions*. Cryobiology, 1987. 24: 196-213.
Fahy, et al., *Vitrification as an approach to cryopreservation*. Cryobiology, 1984. 21: 407-426.
Fahy, et al., *Improved vitrification solutions based on predictability of vitrification solution toxicity*. Cryobiology, 2004. 48: 22-35.
Jacobsen, et al., *Introduction and removal of cryoprotective agents with rabbit kidneys: assessment by transplantation*. Cryobiology, 1988. 25: 285-299.
Karlsson, J.O. and M. Toner, *Cryopreservation*, in *Principles of Tissue Engineering, Second Edition*, R.P. Lanza, R. Langer, and J. Vacanti, Editors. 2000, Academic Press: San Diego. p. 293-307.
Karow, A.M., Jr, *The organ bank concept*, in *Organ Preservation for Transplantation*, A.M. Karow, Jr, G.J.M. Abouna, and A.L. Humphries, Jr, Editors. 1974, Little, Brown and Company: Boston. p. 3-8.
Kheirabadi, B. and G.M. Fahy, *Permanent life support by kidneys perfused with a vitrifiable (7.5 molar) cryoprotectant solution*. Transplantation, 2000. 70(1): 51-57.
Khirabadi, B.S. and G.M. Fahy, *Cryopreservation of the mammalian kidney. I. Transplantation of rabbit kidneys perfused with EC and RPS-2 at 2-4°C*. Cryobiology, 1994. 31: 10-25.
Kheirabadi, B.S., G.M. Fahy and L.S. Ewing, *Survival of rabbit kidneys perfused with 8.4 M cryoprotectant*. Cryobiology, 1995. 32:543-544.
Kheirabadi, B.S., F. Arnaud and E. Kapnik, *The effect of vitrification on viability of rabbit renal tissue*. Cryobiology, 1998. 37: 447.
Kheirabadi, B.S., G.M. Fahy, J. Saur and H.T. Meryman, *Perfusion of rabbit kidneys with 8 molar cryoprotectant (V52)*. Cryobiology, 1993. 30: 611-612.
Kheirabadi, B.S., G.M. Fahy, P. Nannini, J. Saur and H.T. Meryman, *Life support function of rabbit kidneys perfused with 8 molar cryoprotectant*. Cryobiology, 1993. 30: 612.
Kheirabadi, B.S., G.M. Fahy, J. Saur, L. Ewing and H.T. Meryman, *Failure of rabbit kidneys to survive chilling to -30° C. after perfusion with 8 M cryoprotectant at -3° C*. Cryobiology, 1994. 31: 596-597.

(Continued)

*Primary Examiner* — Allison Ford
(74) *Attorney, Agent, or Firm* — Finnegan, Henderson, Farabow, Garrett and Dunner, LLP

(57) ABSTRACT

Methods and compositions are provided for the cryopreservation of human organs and tissues. In certain embodiments, Step 1 comprises perfusion with a vitrifiable cryoprotectant solution at a temperature above −10° C. for a time insufficient for the approximate osmotic equilibration of the organ with the solution, followed by cooling the organ to below −10° C. by perfusion with said solution at a reduced temperature. In certain embodiments, Step 2 comprises increasing the concentration of cryoprotectant further at a temperature from −10 to −40° C. In certain embodiments, Step 3 comprises cooling and vitrifying the organ, rewarming it, and perfusing the organ with a vitrifiable concentration of cryoprotectant whose temperature is either raised gradually or is held at ≥−15° C. Compositions are provided that allow safe organ perfusion with vitrifiable media at >−10° C. and almost complete avoidance of chilling injury at −20 to −25° C. and that allow slow warming after vitrification without freezing.

42 Claims, 11 Drawing Sheets

(56) References Cited

OTHER PUBLICATIONS

Kheirabadi, B.S., G.M. Fahy, L. Ewing, J. Saur and H.T. Meryman, *100% survival of rabbit kidneys chilled to -32° C. after perfusion with 8 M cryoprotectant at -22° C*. Cryobiology, 1994. 31:597.

Pegg, D.E., *Banking of cells, tissues, and organs at low temperatures*, in *Current Trends in Cryobiology*, A.U. Smith, Editor. 1970, Plenum Press: New York. p. 153-180.

Pegg, D.E., *Theory and experiments towards subzero organ preservation*, in *Organ Preservation*, D.E. Pegg, Editor. 1973, Churchill Livingstone: London. p. 108-122.

Pegg, D.E. and M.P. Diaper, *The mechanism of cryoinjury in glycerol-treated rabbit kidneys*, in *Organ Preservation, Basic and Applied Aspects*, D.E. Pegg, I.A. Jacobsen, and N.A. Halasz, Editors. 1982, MTP Press, Ltd: Lancaster. p. 389-393.

Rall, W.F. And G.M. Fahy, *Ice-free cryopreservation of mouse embryos at -196° C. by vitrification*. Nature, 1985. 313:573-575.

Starzl, T.E., *A look ahead at transplantation*. Journal of surgical research, 1970. 10:291-297.

Wang, X., H. Chen, H. Yin, S. Kim, S. Lin Tan, and R. Gosden, *Fertility after intact ovary transplantation*. Nature, 2002. 415: 385.

International Search Report for PCT Patent Application No. PCT/US04/30544.

Supplementary European Search Report for EPO Patent Application No. EP 04784413.

\* cited by examiner

METHODS AND COMPOSITIONS FOR THE CRYOPRESERVATION OF ORGANS

RELATED APPLICATIONS

This application claims priority under 35 U.S.C. 119 to U.S. Provisional Application Ser. No. 60/503,551, filed Sep. 16, 2003, the entire contents of which are hereby incorporated by reference herein.

FIELD OF THE INVENTION

This invention is related to compositions and methods for the cryopreservation of organs.

BACKGROUND OF THE INVENTION

One of the greatest challenges in cryobiology is the cryopreservation of entire organs. Although difficult, this goal is important [14, 15, 24, 25, 28, 29], in part because present limits on human organ storage times after procurement for transplantation substantially reduce the effectiveness and increase the cost of organ replacement [15]. These problems could be eliminated if organs could be banked [9, 24, 25] and stored for times that are shorter than current organ recipient waiting times. Although organ cryopreservation has usually been conceptualized as a way of facilitating the replacement of vital organs by allografts or xenografts, there is also considerable current interest in using the technique to preserve gonads during chemotherapy and then return them to the donor after the completion of treatment [29]. Indefinite-term cryopreservation is probably also essential for solving the largest problem in transplantation medicine, which is the shortfall in organ availability in relation to the total number of transplants that are needed. To address this need, a multi-billion dollar investment in the field of tissue engineering has been made [23], but this approach will also require cryopreservation in order to achieve inventory control and efficient supply chain management of the tissue-engineered products [13].

The cryopreservation of organs was first seriously investigated in the 1950s as a result of the rediscovery of the cryoprotective properties of glycerol by Polge, Smith, and Parkes in 1949. Until 1981, it was assumed that freezing was the only option for cryopreservation, but in 1981, Fahy introduced the radically different concept of vitrification, in which no ice is allowed to form in the organ during either cooling or warming, thus eliminating mechanical injury from ice. In 1985, Rall and Fahy [27] coined the term "vitrification solution," which is a cryoprotectant solution concentrated enough to permit vitrification on cooling and, preferably, no devitrification (freezing) on rewarming after previous vitrification. Although it is thought that any aqueous sample that can be cooled at ultrarapid rates can be vitrified in principle, in the context of organ vitrification, or even in the context of the vitrification of small biological systems like embryos that are to be cooled and warmed in containers, a vitrification solution must be concentrated enough to vitrify when cooled at, generally, less than 3,000° C./min.

Human kidneys, for example, can be cooled no more rapidly than 2° C./min in their core, and for such a case a vitrifiable concentration of cryoprotectant would be defined as a concentration that allows vitrification in a kidney-sized object cooled at 2° C./min or less. Generally, "vitrification" in this context means that no, or at most very few, visible ice crystals would form in such a volume on cooling. Means of cooling organs more rapidly by vascular perfusion with cold heat exchange media would relax the definition of "vitrifiable concentration" to slightly lower concentrations, but very high concentrations would still be required. Moreover, in the context of organ vitrification, it will generally be true that a vitrifiable concentration that does not permit the complete or near-complete suppression of devitrification on rewarming at practicable warming rates will not be useful because devitrification on warming may be unacceptably damaging. As used herein, a "vitrifiable concentration" is defined as a concentration that is capable of allowing vitrification at a cooling rate of ≤20° C./min as judged by visual absence of ice in a 10 ml sample after cooling to below the glass transition temperature ($T_g$) or by absence of detectable exotherms when the solution is cooled to below $T_g$ in a differential scanning calorimeter (DSC).

Since the introduction of the concept of organ vitrification, many advances have been made in the art. However, as of 2004, 23 years have passed since the concept of organ vitrification was first suggested [3], and 19 years have passed since the first proof-of-principle experiment was published showing that mammalian embryos can be vitrified and rewarmed with high survival [27], yet the original goal of successfully vitrifying organs remains elusive.

Processes related to the cryopreservation of organs, including methods and compositions for the introduction and removal of vitrifiable concentrations of cryoprotective agents, have been described in the prior art. For example, U.S. Pat. Nos. 5,723,282 and 5,962,214 claim the following method for preparing organs, tissues, or cells for vitrification:

a) cryoprotectant concentration is gradually elevated to a first concentration while the temperature is mildly reduced;

b) the first concentration is maintained for a sufficient time to permit the approximate osmotic equilibration of the organ or tissue (defined as <50-200 mM difference between arterial and venous concentrations for organs) to occur;

c) concentration is raised to a first intermediate concentration that is not sufficient to permit vitrification (is not vitrifiable);

d) the first intermediate concentration is maintained for a sufficient time to permit the approximate osmotic equilibration of the organ or tissue with the non-vitrifiable intermediate concentration (<50-200 mM difference between arterial and venous concentrations for organs);

e) the temperature is further reduced; and f) the concentration of cryoprotectant is increased to a level sufficient for vitrification, or to a level still insufficient for vitrification followed by an additional cooling step and a final step of increasing concentration to a final, vitrifiable concentration.

U.S. Pat. Nos. 5,821,045 and 6,187,529 claim a method in which a previously cryopreserved organ is:

a) warmed without perfusion to a temperature high enough to permit reperfusion of the organ wherein damage is minimized, and then b) perfused directly with a composition comprising a non-vitrifiable concentration of cryoprotectant that is less than the concentration of cryoprotectant used for cryopreservation, and further comprising one or two osmotic buffering agents, where an osmotic buffering agent is defined as an extracellular solute that counteracts the osmotic effects of greater intracellular and extracellular concentrations of cryoprotectants during the cryoprotectant efflux process. When a liver is being treated, osmotic buffering agents are omitted, but step b) still requires perfusing the liver with a non-vitrifiable concentration of cryoprotectant immediately after attaining the target reperfusion temperature. According to the process limits of the prior art, the concentration during step b) is limited to 20-40% w/v or to about 3-6M, or 60% of the highest concentration perfused.

Clearly, the prior art of adding and removing cryoprotectants and for cooling and warming has proven inadequate for organs as evidenced by the lack of any actual demonstrated success after cooling organs to cryogenic temperatures and rewarming them. Thus, while U.S. Pat. No. 6,395,467 B1 and U.S. patent application Ser. No. 09/916,396 provide extraordinary vitrification solutions and an excellent carrier solution for enhancing their effectiveness, there is still a need in the art for further improvements in the methods and compositions employed for adding and removing cryoprotectants and for cooling and warming organs and tissues.

SUMMARY OF THE INVENTION

In accordance with the present invention, there are provided superior new methods for cooling, cryoprotecting, rewarming, and reperfusing organs and tissues. The present invention extends the teachings of the prior art by providing even more extraordinary and unprecedentedly effective vitrification solutions. It is, therefore, a purpose of the present disclosure to describe new methods and compositions capable of allowing organs to survive and provide life support after cryopreservation by vitrification and transplantation.

Organ vitrification requires the use of a perfusion solution that is sufficiently stable against ice formation (sufficiently able to resist both ice nucleation and ice crystal growth) to allow ice formation to be prevented or adequately limited during the cooling and warming of an organ after perfusion with the solution. Solutions having the required stability, however, tend to be toxic when perfused at 0° C., thus, to reduce the toxicity, perfusion below 0° C. is often desirable. In accordance with one aspect of the present invention, an especially advantageous solution (referred to herein as M22) has been developed. M22 is characterized by the simultaneous presence of dimethyl sulfoxide, ethylene glycol, formamide, N-methylformamide, 3-methoxy-1,2,propanediol, polyglycerol, polyvinyl alcohol or a polyvinyl alcohol-polyvinyl acetate copolymer, and low molecular mass polyvinylpyrrolidone, wherein the solution is sufficiently concentrated to remain ice-free based on differential scanning calorimetry when vitrified and then rewarmed at less than 1° C./min. Although the composition can vary, as discussed in greater detail herein, in accordance with a presently preferred embodiment of the invention, M22 has a total concentration of about 9.3 molar, or about 64.8% w/v. M22 is so named because it is intended to be exposed to living systems predominantly near −22° C. to minimize the potential for toxicity that may be produced at higher temperatures.

However, there are no methods known in the prior art by which an organ can be continuously perfused starting with no cryoprotectant at above 0° C. and ending with a solution like M22 at −22° C. with subsequent retention of life support capability after transplantation, and there is no guidance in the art about how such a continuous perfusion protocol can be successfully reversed, returning the organ to zero percent cryoprotectant at above 0° C. after prior perfusion at −22° C. Cooling to −22° C. is complicated by the need to avoid so-called chilling injury, which can be defined as injury caused by cooling per se. Directly cooling organs perfused with 7.5M to 8M cryoprotectant from −3° C. to −30° C. produced marked injury [21], consistent with earlier observations on kidneys perfused with other cryoprotectants and cooled to higher subzero temperatures [12, 26]. This phenomenon is also readily detectable in renal cortical slices [11]. Although it was found that this injury could be avoided by cooling to about −24° C. in the presence of only 6.1M cryoprotectant [11, 22], this approach was later found to result in so much more chilling injury when additional cryoprotectant was added and the temperature was further reduced as to be worse than simple cooling from 0° C. [18]. A completely different and far superior method of avoiding chilling injury was later put forward (U.S. patent application Ser. No. 09/916,032), but this method does not provide explicit means for applying the technique to whole organs. Furthermore, the method for avoiding chilling injury does not include critically important methods for rewarming organs after prior cooling and for reperfusing them in such a way as to avoid damage following exposure to vitrifiable concentrations of cryoprotectant such as M22.

In accordance with the present invention, new processes have been discovered that overcome all of these problems and are highly advantageous for the introduction and washout of cryoprotectants and for cooling and warming organs during continuous perfusion.

Invention methods for cooling, stabilizing, rewarming, and diluting cryoprotectants in perfused organs have been successfully tested using M22 as a model solution as described in the Examples given below, but will be equally applicable to any solution intended for the vitrification of whole organs. They are not restricted to the rewarming and dilution of organs following perfusion above −15° C. and will in fact be particularly helpful following the perfusion of organs at temperatures of −15° C. and below, and still more helpful following the perfusion of organs at temperatures between −20° C. and −30° C. They are not restricted to the safe cooling of organs to −15° C. or above, but are particularly helpful for the safe cooling of organs to −15° C. or below, and particularly for the safe cooling of organs to −20° C. to −30° C. They have been shown to be compatible with the survival and life support function of a mammalian organ after vitrification and rewarming, an accomplishment not previously achieved. Although the invention is specifically directed toward organs perfused primarily through the vascular system (perfusion through internal cavities other than blood vessels, such as the chambers of the heart or the ventricles of the brain is also included within the scope of the invention, usually as a supplement to vascular perfusion), the same concentration-time-temperature protocols can also be effectively applied to unperfused tissues treated with cryoprotectants by immersion or superfusion.

BRIEF DESCRIPTION OF THE FIGURES

FIG. 2A illustrates the occurrence of injury on slices transferred to −20° C. at the stated tonicity. FIG. 2B presents a comparison of constant-tonicity protocols to non-equilibrium tonicity protocols. Slices transferred under constant isotonic conditions (1×→1×) experienced considerable damage, slices transferred under constant hypertonic conditions (2×→2×) sustained practically no injury, and slices equilibrated under isotonic conditions (1×) at 0° C. and transferred to a twiceisotonic (2×) precooled solution at −20° C. (1×→2×) showed injury intermediate between the 1×→1× and the 2×→2× treatments.

FIG. 3A also establishes the lack of toxicity of VMP at −3° C., and provides a useful data format for later figures. All complete data sets are plotted horizontally against a common time base in three separate panels (upper, middle, and lower). More focused attention is given to narrow time range data in the insets. All insets show response vs. time plots.

FIG. 3A, Upper panel: arterial molarity (M; heavy line) and the arteriovenous concentration difference across the kidney (A-V) in molar (M) units. (Note: upon switching to 0 mM cryoprotectant, the display mode changes to plot the concentration of mannitol being perfused, causing an apparent increase in concentration on the record.)

FIG. 3A, Middle panel: arterial (heavy line) and venous temperatures (T) in ° C. as measured using an arterial in-line needle thermocouple and a second fine thermocouple inserted directly in the venous effluent underneath the kidney.

FIG. 3A, Lowest panel: arterial perfusion pressure (P) in mmHg and perfusate flow rate (heavy line) in ml/min per gram of post-flush, pre-perfusion kidney weight. Perfusion pressure was divided by 40 to permit it to be plotted on the same scale as the flow rate. Prior to introducing cryoprotectant, the perfusate was TransSend-B ([10], and formula 7 of [7]) plus 2% hydroxyethyl starch (HES, of relative molecular mass $M_r$~450 kilodaltons, obtained from B. Braun, Irvine, Calif.). As VMP was introduced (VMP molarity plotted in upper panel, heavy line; VMP prepared in LM5 carrier), the HES and TransSend-B were diluted gradually to zero. This procedure was followed in all perfusions. VMP was washed out initially with 3% HES plus 300 mM mannitol using half-strength VMP in LM5. As washout proceeded, the carrier solution was gradually transitioned back from LM5 to TransSend-B. Note that at the end of the VMP plateau, sufficient time has been allowed for approximate osmotic equilibration of the organ with VMP as indicated by an A-V difference of only 50 mM (middle inset in middle panel). Upper right inset: postoperative serum creatinine levels (Cr); "Day" refers to postoperative day; time zero Cr values represent serum creatinines at nephrectomy and at transplant. Upper left inset: "URI" refers to urine refractive index and is plotted against the duration of VMP perfusion.

DETAILED DESCRIPTION OF THE INVENTION

Figure 1:
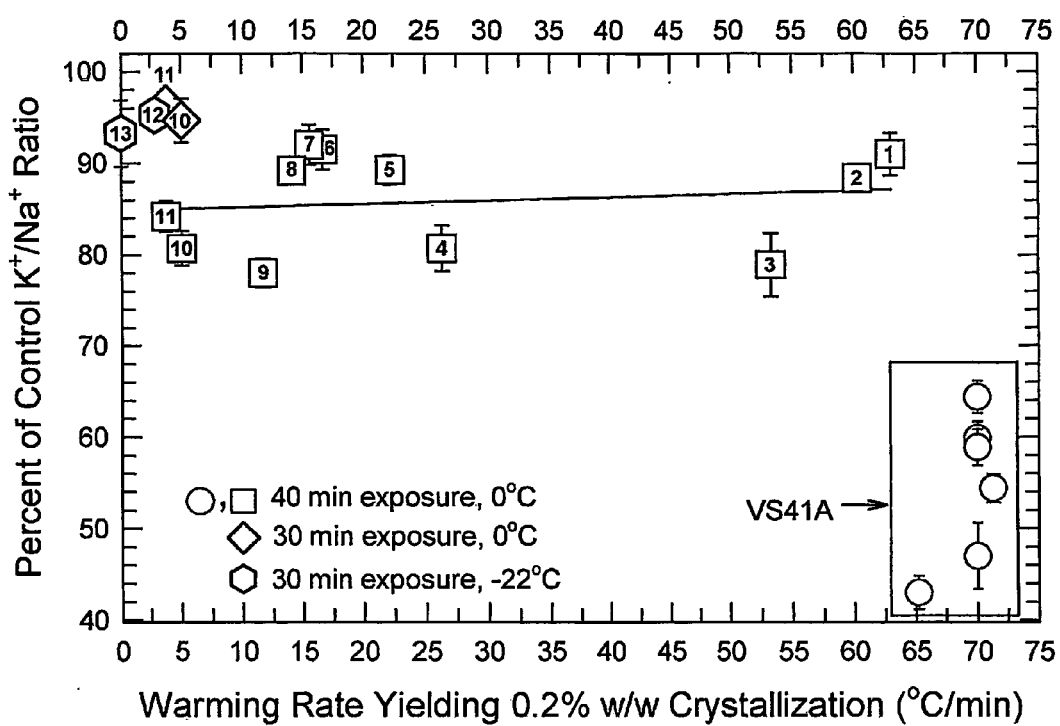
FIG. 1 presents a "Viability-stability plot" for rabbit renal cortical slices exposed to the vitrification solutions described in Tables 1 and 2.

In accordance with one embodiment of the present invention, there are provided methods for the cooling of organs from a temperature above −10° C. to a desired low temperature below −10° C. by continuous vascular perfusion with minimal injury, the methods comprising:

perfusing the organ with a cryoprotectant solution (e.g., a first mixture of permeating and non-permeating cryoprotectants having a freezing point lower than the said desired low temperature) for a time insufficient to permit the approximate osmotic equilibrium of the organ with said mixture of cryoprotectants to take place;

lowering the temperature of the arterial perfusate to or below the said desired low temperature; and continuing to perfuse said mixture until the temperature of at least a portion of the organ is considered to reach the target temperature.

An exemplary first mixture of permeating and non-permeating cryoprotectants, VMP, which can be effectively used in the above-described method is as follows. VMP is usually prepared in a carrier solution whose tonicity in the absence of the cryoprotectants of VMP is defined to be isotonic, or 1× isotonic. VMP in the carrier solution LM5 (the composition of which is provided in [5, 10] and in the footnotes of Table 1) has an effective tonicity of 1.2 times isotonic, where tonicity is defined as the ratio of the osmolality of the components of VMP minus the permeating cryoprotectants (permeating cryoprotectants defined as those cryoprotectants whose molecular mass is less than 150 daltons) to the osmolality of the cryoprotectant-free carrier solution (preferably, the solution known as LM5). The increase in tonicity over isotonic is due to the presence in VMP of two antinucleating agents or "ice blockers," polyglycerol (sometimes referred to as PGL or "Z-1000") and polyvinyl alcohol or a copolymer of polyvinyl alcohol and polyvinyl acetate (sometimes referred to as PVA or "X-1000") of mass >150 daltons. Including the ice blockers in VMP provides protection from chilling injury during cooling of the organ to −15 to −40° C. and also provides more time for these polymers to permeate through the extracellular spaces, including cavities such as urinary spaces or ventricles, of the organ, thus further ensuring their adequate distribution prior to vitrification.

The non-ice-blocker components of VMP can each vary by ±25% without loss of the effectiveness of the VMP variant solution. VMP can also be modified to include other polymers intended to contribute to ice blocking or ice growth inhibiting properties of the subsequently-perfused primary or final vitrification solution, and can optionally include slightly (0-50% more) concentrated carrier solution provided the desirable tonicity of the modified VMP in carrier solution, as elevated by the sum of the presence of the ice blockers, the other polymer(s) intended to inhibit ice growth, and more than an isotonic amount of carrier solution, has a tonicity usually within the generally more preferred range of 1.1 to 1.6 times isotonic. In other words, the overall most preferred mixture of permeating and non-permeating cryoprotectants (in carrier solution) for use in this method has a tonicity after full equilibration with living cells, tissues or organs that ranges from approximately 1.1 to about 1.6 times isotonic. The total amount of ice blocker in VMP can be varied from 0% to about 7% w/v, consistent with the above tonicity limitations, but the most preferred amount is 1-4% w/v. Typically, the desired low temperature below −10° C. will range from about −15° C. to about −40° C., and is most preferably from about −20° C. to −30° C.

The perfusion pressure during the above-described method may be constant or variable but should be within about 40-110 mmHg, or more preferably within about 50-90 mmHg or still more preferably within about 55-85 mmHg. In one variant of the method, the perfusion pressure is at 40±8 mmHg before cooling and is elevated to 50-80 mmHg during cooling. The desirable perfusion pressure range for larger organs will be higher than for smaller organs, and may range from 50-110 mmHg, or more preferably from 60-100 mmHg. As used in this specification, "arterial" means "flowing into the organ," and is intended to include perfusion of the liver via the portal vein and retrograde perfusion of organs through their veins.

In accordance with another embodiment of the present invention, there are provided methods for warming organs from below −10° C. to a desired high temperature of −10° C. or above by continuous vascular perfusion with minimal injury, the methods comprising:
  raising organ temperature by raising the temperature of the arterial perfusate to or above the desired high temperature without changing arterial concentration and while continuing to perfuse the organ; and
  continuing to perfuse the organ without changing arterial concentration until the organ temperature reaches the desired high temperature.

Typical desired high temperatures will range from about −9.9° C. to about +5° C., the most preferred range being −8° C. to −2° C. The organ is optimally considered to have reached the desired high temperature when the coldest parts of the organ are sufficiently close to the desired high temperature to minimize injury upon subsequent dilution of the cryoprotectant while also minimizing toxicity caused by delaying dilution. This method can be used for warming organs containing non-vitrifiable concentrations of cryoprotectant and for organs containing vitrifiable concentrations of cryoprotectant that can vitrify at cooling rates of 20° C./min or below. In the latter case, the organ is perfused for a time with vitrifiable media at the desired high temperature or above before any subsequent dilution. In this method, no inclusion of osmotic buffering agents in a diluent is involved due to the lack of cryoprotectant dilution in the warming method.

In accordance with yet another embodiment of the present invention, there are provided methods for perfusing organs with a vitrifiable concentration of cryoprotectant, wherein the organ is first cooled by the cooling method described above, to the desired low temperature below −10° C. and the organ is then perfused with the vitrifiable concentration of cryoprotectant. As used herein, the word "cryoprotectant" is generic and can refer to a mixture of individual cryoprotectants of both low (<100-200 daltons) and high (≥150 daltons) mass. The phrase "vitrifiable concentration of cryoprotectant" as employed herein refers to a concentration that will allow regions of the organ that are saturated with the cryoprotectant to vitrify when the organ is cooled at a rate of 20° C./min or below. A particularly preferred solution for use in this method contains DMSO, formamide, ethylene glycol, more than 1% w/v polyglycerol, polyvinylalcohol, polyvinylpyrrolidone, N-methylformamide, and 3-O-methyl-rac-glycerol. A specific embodiment of this solution is the formula known as M22 whose composition is disclosed herein (see Table 2). The components of M22 can be varied by ±25% without loss of effectiveness of the resulting M22 variants in this method. Also, M22 can be modified to contain polyethylene glycol, preferably at a concentration of about 0.5-4% w/v.

Also in this method, the perfusion can be conducted at a first pressure, which can be about 40 mmHg, before perfusion with said vitrifiable concentration of cryoprotectant and can be raised to a second pressure, which is preferably 41-110 mmHg, and most preferably to 55-85 mmHg, when perfusion with said solution begins. Constant pressure perfusion within the range of 32-110 mmHg can also be effective in accordance with the present invention.

In accordance with still another embodiment of the present invention, there are provided methods for initially diluting cryoprotectants in organs previously perfused with cryoprotectant at a temperature of −10° C. or below, the methods comprising:
  raising the arterial perfusate temperature to or above a desired high temperature above −10° C. during perfusion of the organ without changing the concentration of cryoprotectant;
  continuing to perfuse the organ without changing cryoprotectant concentration for a time that is sufficiently long to protect the organ from injury resulting from subsequent perfusate dilution but not so long as to cause undesired injury from continued exposure to the said undiluted cryoprotectant at the desired high temperature; and
  diluting the cryoprotectant.

Typically, the time that is sufficiently long to protect the organ from osmotic dilution injury but not so long as to cause undesired injury from exposure to the solution at the desired high temperature is 1 to 10 minutes. In a variation of this method, perfusion below −10° C. can be interrupted for example by disconnecting the organ from the perfusion machine, and the arterial perfusate can be warmed to the desired high temperature above −10° C. while the organ remains disconnected and unperfused, after which the organ can be reattached to the perfusion machine and perfused with arterial perfusate at the desired high temperature.

In either variant method, perfusion pressure at the onset of, during, or after cryoprotectant dilution can be lowered to a pressure below that used during perfusion below −10° C. and before the onset of perfusion temperature elevation and/or the onset of dilution. In a presently preferred embodiment, the lowered perfusion pressure is preferably in the range of 40-85 mmHg.

In either variant method, a preferred means of dilution is to use a diluent that contains no added osmotic buffers. The solution known as VMP, which contains only permeating and non-permeating cryoprotectants and no osmotic buffers, is a useful prototypical diluent for use in the described dilution method. The method is particularly useful when the concentration perfused below −10° C. and at the desired high temperature above −10° C. before dilution is vitrifiable at a cooling rate of 20° C./min or less, and preferably at a cooling rate of 2° C./min or less. Further, the dilution step can be conducted using a concentration of cryoprotectant that is lower than the highest concentration added at below −10° C. but still high enough to be vitrifiable at a cooling rate of ≤20° C./min.

In accordance with still another embodiment of the present invention, there are provided methods for diluting cryoprotectant in and warming organs from below −10° C. to a desired high temperature of −10° C. or above by continuous vascular perfusion with minimal injury, the methods comprising:
  raising the temperature of the arterial perfusate to or above the said desired high temperature while continuously perfusing the organ; and
  simultaneously reducing arterial concentration while the organ temperature is rising toward said desired high temperature during continuous arterial perfusion of the organ.

Typically, the desired high temperature contemplated for use in this method will range from about −9.9° C. to about 0° C., the most preferred range being −8° C. to −2° C. Typically in this method the concentration of the arterial perfusate is lowered by 0.5-1.5 molar while temperature is raised from a temperature below −10° C. to a temperature above −10° C. Also typically in this method, the warming rate from below −10° C. to above −10° C. is between 0.5° C./min and 20° C./min and is preferably greater than 1° C./min, with two satisfactory rates being about 2° C./min and about 10° C./min. Typically, the rate of arterial concentration dilution during warming from below −10° C. to above −10° C. is between 50 mM/min and 1000 mM/min. This method of simultaneous perfusion warming and perfusion dilution can be effectively and desirably accomplished without the inclusion of osmotic buffering agents during dilution of the cryoprotectant. The reduction of cryoprotectant concentration in this method need not result in a final concentration that is non-vitrifiable. Desirably in the method, cryoprotectant concentration is reduced to a level that is still vitrifiable.

In accordance with a still further embodiment of the present invention, there are provided methods wherein an organ is perfused with a solution capable of allowing the organ to vitrify when the organ is cooled at a rate of 20° C./min or less at the desired low temperature at or below −10° C. according to the cooling method described above but further comprising:
  interrupting continuous perfusion at the desired low temperature, and;
  cooling the organ to a temperature below the said desired low temperature at or below −10° C.

Interruption of perfusion as contemplated herein may continue until the organ is rewarmed to a temperature sufficiently high to allow the organ to be perfused at an arterial perfusate temperature equal to or greater than the said desired low temperature. The interruption of perfusion may also continue while the organ is stored at a temperature below the desired low temperature. In addition, the interruption of perfusion prior to cooling can occur after a previous perfusion time insufficient to permit the approximate osmotic equilibration of the organ. In addition, the organ can be vitrified by cooling following perfusion with said solution capable of allowing the organ to vitrify when the organ is cooled at a rate of 20° C./min or less at the said desired low temperature at or below −10° C. for a time insufficient to permit the approximate osmotic equilibration of the organ with said solution.

In accordance with yet another embodiment of the present invention, there are provided methods of diluting cryoprotectant in an organ after the organ has been perfused at a temperature below −10° C., the methods comprising:
  warming the organ externally; and
  perfusing the organ at an arterial temperature equal to or above a desired high temperature of ≥10° C. with a reduced concentration of cryoprotectant that does not contain a non-penetrating osmotic buffering agent.

In this method, the reduced concentration of cryoprotectant can be either non-vitrifiable (for organs other than the liver) or vitrifiable (for all organs).

Invention methods and compositions will now be described in greater detail with reference to the following non-limiting Examples that describe each inventive component of the invention, as follows.

Example 1

M22 and Other Preferred Vitrification Solutions

Figure 5:
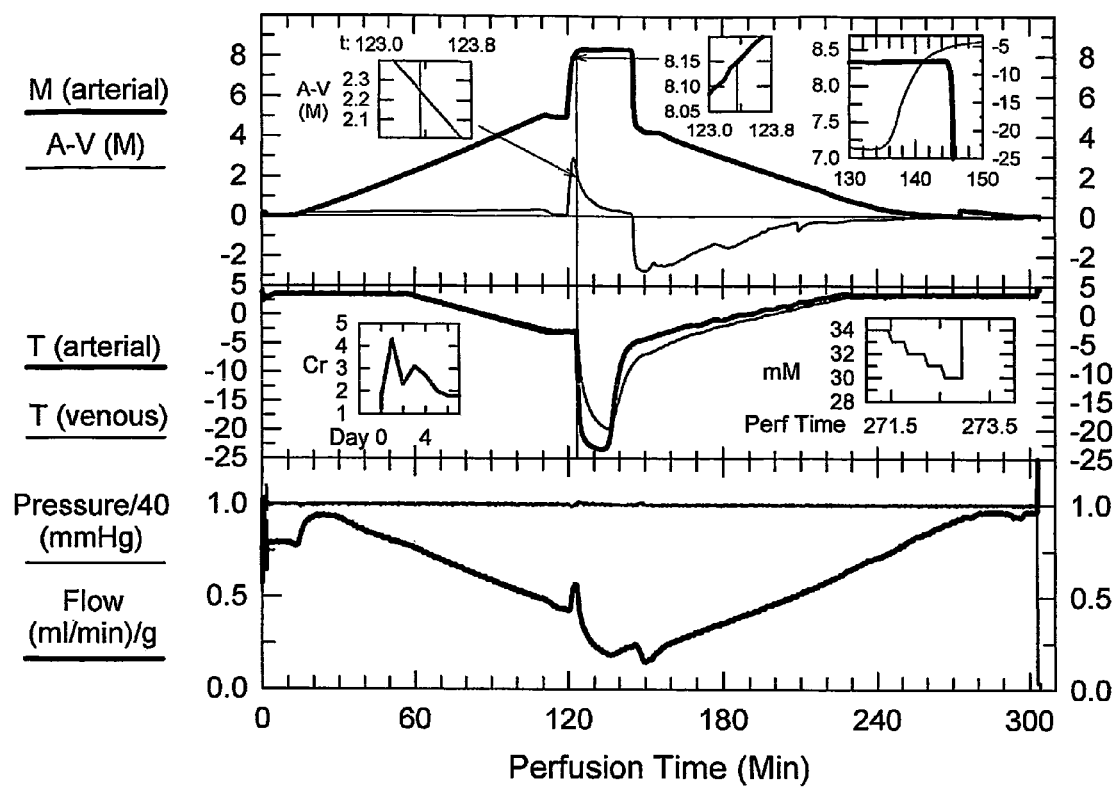
FIG. 5 describes a specific experiment showing an exemplary continuous perfusion protocol according to the present invention for cooling after insufficient time for approximate osmotic equilibrium between the organ and the perfusate prior to cooling, with warming by reperfusion with a concentration not less concentrated than the concentration present below −15° C. The left upper inset shows that at the time of onset of cooling (marked by the vertical line), nominally 5 min after the onset of VMP perfusion, the A-V concentration difference was extreme at about 2.25M, which is very far from approximate osmotic equilibrium. The middle upper inset shows that at this time, not only the venous concentration but also the arterial concentration (plotted on a molar concentration scale) has failed to reach the target 8.4M concentration of VMP, arterial concentration having reached only 8.15M. This emphasizes the nominal nature of organ perfusion protocols, in which programmed step changes in time and temperature do not necessarily occur instantaneously. For this reason, both literal and non-literal interpretation of process descriptions such as "perfuse VMP for 5 min" are appropriate, not just literal interpretations. The right upper inset illustrates the method of constant-concentration continuous perfusion-rewarming (perfused arterial molarity indicated by heavy line and left vertical axis, arterial perfusate temperature indicated by the light line and right vertical axis). Before warming, the organ is already at a temperature permitting reperfusion of the organ wherein damage is minimized (~−23° C.), but it is not perfused with non-vitrifiable solution containing osmotic buffers at −20° C. Instead, it is perfused with rapidly warming, undiluted, vitrifiable, and osmotic buffer-free solution until the arterial temperature exceeds −10° C. and approaches −5° C., and only then is perfused with more dilute, non-vitrifiable solution. The left and right insets in the middle panel represent postoperative creatinine levels and the concentrations of cryoprotectant being perfused just before switching to an entirely cryoprotectant-free perfusate, respectively.

Several preferred solutions of utility in the present invention are described in Table 1, and their effects on ice formation and kidney slice viability are described in FIG. 1. In this type of plot, the biological recovery of the system after exposure to a vitrification solution is plotted against the critical warming rate of the tested vitrification solution. In this figure, the critical warming rate was defined as the rate that was sufficient to suppress crystallization of all but 0.2% of the test solution mass, as measured by the mean enthalpy of melting of triplicate samples cooled and warmed in a differential scanning calorimeter (DSC). The numbers inside the plotted symbols refer to the numbers of the corresponding solutions listed in Table 1, except that point 13 refers to data obtained for a new solution, M22, whose formula is provided in Table 2. Viability is assessed using the steady-state $K^+/Na^+$ ratio achieved by the slices after cryoprotectant washout and 90 min of incubation at 25° C. followed by washout of most extracellular cations with isotonic mannitol [2, 4, 8]. The methods used for addition and washout of cryoprotectant are believed to avoid osmotic injury and allow only the intrinsic effects of the tested solutions to be measured, and follow the basic methodology of FIG. 5 or 7 below but without perfusion.

The preferred methodology of the present invention is illustrated below using examples involving the particularly preferred M22 vitrification solution and the VMP transitional solution. FIG. 1 shows the position of M22 as a particularly advantageous new vitrification solution. One of the advantages of M22, as noted above, it that it has a very low critical warming rate. The critical warming rate, referred to here as $v_{WCR}$, is defined here as the warming rate needed to adequately or fully suppress detectable crystallization. FIG. 1 plots the recovery of functionality of rabbit renal cortical slices against the $v_{WCR}$ of the solution to which they were exposed (Table 1). Data for exposure to the prior art solution known as VS41A or VS55, which consists of 3.1M dimethyl sulfoxide plus 3.1M formamide plus 2.6M 1,2-propanediol, are included as a point of reference (circles). As can be seen, by judicious selection of compositional factors and exposure conditions, it is possible to travel closer and closer to, and perhaps even to literally reach, a solution that does not devitrify (critical warming rate, ~0° C./min) while retaining high functional viability. For example, adding 0.5% w/v of each of the antinucleators ("ice blockers") polyvinyl alcohol (PVA) and polyglycerol (PGL) and changing the carrier solution from a high glucose to a lower glucose carrier known as LM5 (see Table 1) Cut $v_{WCR}$ from about 26° C./min to about 12° C./min (point 9 vs. point 4) with no penalty in toxicity. The same maneuver plus the replacement of PVP K30 with PVP K12 lowered $v_{WCR}$ from 63° C./min to 14° C./min (point 8 vs. point 1). Elevating the ice blockers by another 0.5% w/v each and increasing permeating cryoprotectant level by 1% w/v (point 11 vs. point 8) yielded an additional 3.7-fold gain with, again, no reduction in functional recovery. Overall, compared to VS41A, the use of ice blockers, PVP K12, and LM5 in combination with permeating cryoprotectant mixtures based on the combination of dimethyl sulfoxide, formamide, and ethylene glycol [10] permits approximately a 20-fold improvement in $v_{WCR}$ with a simultaneous improvement in K$^+$/Na$^+$ ratio from about 55% of control to about 85% of control in slices exposed to the final vitrification solution for 40 min at 0° C. (FIG. 1, squares vs. circles). Reducing exposure by just 10 min, to 30 min, resulted in still less toxicity (diamond-shaped points).

TABLE 1

Some Biologically Acceptable, Highly Stable Vitrification Solutions[a]

| Point | Name | $v_{WCR}$ | D | F | E | A | PK30 | PK12 | PVA | PGL | Carrier | % w/v |
|---|---|---|---|---|---|---|---|---|---|---|---|---|
| 1 | $V_{EG}$ – 4% D(1)F + 7PK30 | 63 | 21.671 | 12.492 | 16.837 | 0 | 7 | 0 | 0 | 0 | RPS-2 | 58 |
| 2 | $V_{EG}$ + 1% PVA | 60.3 | 24.208 | 13.955 | 16.837 | 0 | 0 | 0 | 1 | 0 | | 56 |
| 3 | $V_{EG}$ + 2% D | 53.3 | 24.208 | 13.955 | 16.837 | 0 | 0 | 0 | 0 | 0 | RPS-T | 57 |
| 4 | E[D(.7)F]$_{38.16}$ + 6PK12 | 26.3 | 20.926 | 17.234 | 16.840 | 0 | 0 | 6 | 0 | 0 | GHP-2 | 61 |
| 5 | 52% $V_{EG}$S + 6PK12 + 0.5 + 0.5 | 22.2 | 22.887 | 13.194 | 15.919 | 0 | 0 | 6 | 0.5 | 0.5 | LM5 | 59 |
| 6 | 52% $V_{EG}$S + 6PK12 + 1% PVA | 16.7 | 22.887 | 13.194 | 15.919 | 0 | 0 | 6 | 1 | 0 | RPS-2 | 59 |
| 7 | 50% $V_{EG}$S + 8PK12 + 1% PVA | 15.6 | 22.007 | 12.686 | 15.307 | 0 | 0 | 8 | 1 | 0 | RPS-2 | 59 |
| 8 | $V_{EG}$ – 4% D(1)F + 7PK12 + .5 + .5 | 14.1 | 21.671 | 12.492 | 16.837 | 0 | 0 | 7 | 0.5 | 0.5 | LM5 | 59 |
| 9 | E[D(.7)F]$_{38.16}$ + 6PK12 + .5 + .5 | 11.7 | 20.926 | 17.234 | 16.840 | 0 | 0 | 6 | 0.5 | 0.5 | LM5 | 62 |
| 10 | $V_{EG}$ – 3% D(1)F + 7A + 1PVA + 4 | 5.1 | 22.305 | 12.858 | 16.837 | 7 | 0 | 0 | 1 | 4 | LM5 | 64 |
| 11 | $V_{EG}$ – 3% D(1)F + 7PK12 + 1 + 1 | 3.8 | 22.305 | 12.858 | 16.837 | 0 | 0 | 7 | 1 | 1 | LM5 | 61 |
| 12 | $V_{EG}$ – 3% D(1)F + 7E + 1PVA + 4 | 2.9 | 22.305 | 12.858 | 23.837 | 0 | 0 | 0 | 1 | 4 | LM5 | 64 |

[a]Solution numbers refer to points in FIG. 1.
$v_{WCR}$ is the warming rate required to suppress ice formation to 0.667 joules/100 g, which is equivalent to the amount of heat that would be produced by the crystallization of 0.2 grams of water per 100 grams of solution at 0° C. $v_{WCR}$ was measured after cooling to –150° C. at 100° C./min.
Cryoprotectant concentrations are given in % w/v (g/dl) units.
Abbreviations:
D = dimethyl sulfoxide;
F = formamide;
E = ethylene glycol;
A = acetol;
PK30 = PVP K30, of Mr 40,000 daltons;
PK12 = PVP K12, of $M_r$ 5000 daltons;
PVA = polyvinyl alcohol or a copolymer of polyvinyl alcohol and polyvinyl acetate, particularly the Supercool X-1000 ice blocker commercially available from 21$^{st}$ Century Medicine (21 CM) in Rancho Cucamonga, California;
PGL = polyglycerol, specifically decaglycerol, particularly the commercially-available Supercool Z-1000 ice blocker from 21 CM;
(1) and (.7) refer to the molar ratio of dimethyl sulfoxide to formamide in the solution;
$V_{EG}$ = a cryoprotectant solution described elsewhere [9, 10] and recapitulated for point 2;
$V_{EG}$S = "$V_{EG}$ Solutes," which refers to the total amount of the sum of the D, F, and E components of $V_{EG}$ (in the proportions found in $V_{EG}$);
the carrier solutions RPS-2, RPS-T, and GHP-2 are described elsewhere [5, 9].
The LM5 carrier solution [5] consists of 90 mM glucose, 45 mM mannitol, 45 mM lactose, 28.2 mM KCl, 7.2 mM K$_2$HPO$_4$, 5 mM reduced glutathione, 1 mM adenine HCl, 10 mM NaHCO$_3$, and, when cryoprotectant is absent, 1 mM CaCl$_2$ and 2 mM MgCl$_2$.
Solution 11 is also known as VM3.
Solution 10 is also known as "1.5X".
The absolute amounts and relative proportions of all components of solutions 1-12 can be varied by ±20% without losing effectiveness in the invention.

TABLE 2

Properties of M22

| Component[1] | Concentration or Property |
|---|---|
| Dimethyl sulfoxide | 2.855 M (22.305% w/v) |
| Formamide | 2.855 M (12.858% w/v) |
| Ethylene glycol | 2.713 M (16.837% w/v) |
| N-methylformamide | 0.508 M (3% w/v) |
| 3-methoxy,1,2-propanediol* | 0.377 M (4% w/v) |
| PVP K12 | 2.8% w/v (~0.0056 M) |
| PVA[a] | 1% w/v[b] (~0.005 M) |
| PGL[a] | 2% w/v[b] (~0.0267 M) |
| 5X LM5[c] | 20 ml/dl |
| Total cryoprotectant concentration | 9.345 M (64.8% w/v) |
| pH | 8.0 |
| Nominal tonicity | 1.5 times isotonic |
| Melting point[d] | ~–54.9° C. (estimated) |
| Critical warming rate | <1° C./min |

[1]The first 5 components listed can be varied by ±25% without losing effectiveness in the invention. The next 3 components (polymers) can be varied up to three fold without losing effectiveness in the invention. However, the amounts of components as listed are the best mode amounts. PVP K12 ~1300-5000 daltons.
*This molecule is also called 3-O-methyl-rac-glycerol.

TABLE 2-continued

Properties of M22

| Component[1] | Concentration or Property |
|---|---|

[a]PVA (also called "Supercool X-1000") and PGL (also called "Supercool Z-1000") are commercially available ice blockers obtainable from 21st Century Medicine, Inc. and consist of a polyvinylalcohol-polyvinylacetate copolymer (in which approximately 80% of the alcohol or acetate moieties are hydroxyl groups and 20% are acetyl groups) and polyglycerol, respectively.
[b]Final polymer concentrations.

TABLE 2-continued

Properties of M22

| Component[1] | Concentration or Property |
|---|---|

[c]1X LM5 (see Table 1 for formula) contains 1 mM CaCl$_2$ and 2 mM MgCl$_2$, but these are omitted from the 5X LM5 to avoid the formation of precipitates. "5X LM5" refers to a 5-fold increase in the molar concentrations of the components of LM5. The use of 5X LM5 is for convenience in preparing the solution but the components of 1X LM5 can be weighed out directly and used instead if desired. Although LM5 is the preferred carrier solution for M22, it is not part of the definition of M22, as M22 can also be made up effectively in other carrier solutions. Also, the amount of 5X LM5, or of dry 1X LM5 components if an LM5 concentrate is not used to prepare the solution, can be varied. Tonicity can be kept constant at 1.5X by increasing the amount of LM5 and decreasing the amount of polymer(s) present (PVP K12, PVA, and PGL), or by reducing the amount of LM5 and increasing the amount of polymer(s) present (see Table 3 for tonicity equivalents of LM5 and polymers). Total solution tonicity can also be varied from 1 to 3 times isotonic. However, 1X LM5 and 1.5 times isotonic are preferred in the best mode invention.
[d]This solution could not be frozen and therefore a theoretical melting point could only be obtained by extrapolation of data for 94% v/v and 97% v/v of full-strength M22. Note: polyethylene glycol (PEG) can also be used effectively in this solution at about 0.5-4% w/v in place of and/or in addition to other polymer (PGL and PVP). PEG of 600 or more daltons is preferred, and especially of 600-4000 daltons.

Finally, exposure at –22° C. for 30 min allowed good recovery (hexagon-shaped points) after exposure to solutions having critical warming rates of about 0 to 2.9° C./min. The point plotted at 0° C./min represents M22. Warming this solution from below its $T_g$ at 1° C./min (the lower warming rate limit of our differential scanning calorimeter) failed to reveal any melting endotherm, and numerous efforts to freeze this solution using various cooling and annealing protocols failed. Clearly, it would be highly desirable to be able to perfuse-kidneys with M22 near −22° C. based on the results of FIG. 1.

Example 2

Figure 2:
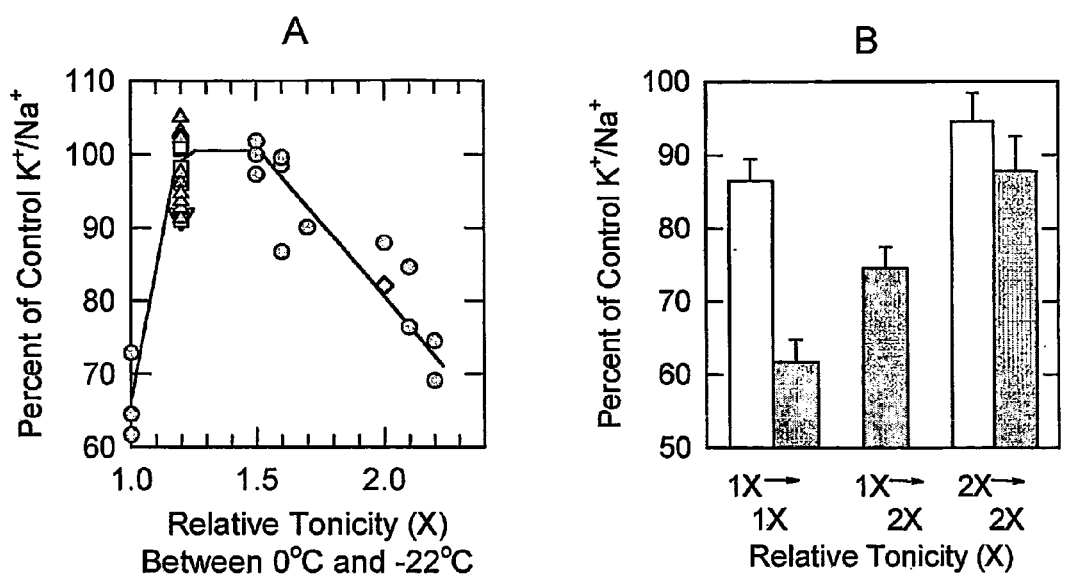
FIG. 2 collectively illustrates hypertonic modification of chilling injury caused by abrupt transfer of slices from solutions at 0° C. to solutions at −20° C.

Method for (1) Safely Cooling Kidneys by Continuous Vascular Perfusion to −20 to −25° C. Without Prior Approximate Osmotic Equilibrium Between the Organ and the Perfusate; (2) Warming by Continuous Vascular Perfusion to a Temperature Above a Temperature Which Permits the Organ to be Perfused, and (3) Perfusing with a Vitrifiable, Unreduced Concentration of Cryoprotectant Containing No Osmotic Buffering Agent The design of the first step of a vitrification process that involves perfusion of a vitrification solution such as M22 at a temperature near −22° C. was based in part on background information on chilling injury in rabbit renal cortex (U.S. patent application Ser. No. 09/916,032, Hypertonic Reduction of Chilling Injury) as illustrated in FIG. 2. According to the data in FIG. 2A, cooling in the presence of an elevated tonicity can prevent chilling injury in rabbit renal cortical slices virtually entirely, with an optimum tonicity of 1.2-1.5 times isotonic. Table 3 provides some useful reference tonicity data and an operational definition of tonicity.

TABLE 3

Some Useful Reference Tonicity Data

| Solution | Osmolality$^a$ | Tonicity $(X)^b$ | Polymer Osmolality$^c$ |
|---|---|---|---|
| LM5 | 283 ± 3 mOsm | 1.0 | — |
| LM5 + 1% Z$^d$ | 321 ± 3 mOsm | 1.13 | Z = 38 mOsm |
| LM5 + 1% X$^e$ | 291 ± 1 mOsm | 1.03 | X = 8 mOsm |
| LM5 + 1% Z + 1% X | 330 ± 3 mOsm | 1.17 | S$^f$ = 46 mOsm |
| LM5 + 7% PVP K12 | 413 ± 2 mOsm | 1.46 | P$^g$ = 130 mOsm |
| LM5 + 7% PVP K12 + 1% Z + 1% X | 474 ± 5 mOsm | 1.67 | S = 191 mOsm |
| LM5 + 2% Z + 1% X + 2.8% PVP K12 | 421 ± 3 mOsm | 1.49 | S = 138 mOsm |

$^a$Mean ± ½ the range of the mean.
$^b$Tonicity relative to LM5. Tonicity is defined as $\pi_{Test}/\pi_{iso}$, where $\pi_{Test}$ = the osmolality of the cryoprotectant-free test solution (made by adding nominal impermeants to the baseline, cryoprotectant-free carrier solution) and $\pi_{iso}$ = the osmolality of the baseline carrier solution (in this case, the osmolality of LM5, i.e., 283 mOsm). It is assumed that all carrier solution components are impermeant for practical purposes. It is further assumed that the presence of permeating cryoprotectants has no practically relevant effect on the effective tonicity of the solution. It is further assumed that all solutes having a mass of ≥150 daltons are nominally impermeant.
$^c$Mean osmolality minus 283 mOsm.
$^d$Z = Supercool Z-1000 (1% refers to 1% w/v of polyglycerol, not 1% of the commercially-available stock 40% w/w solution).
$^e$X = Supercool X-1000 (1% refers to 1% w/v of polyvinyl alcohol, not 1% of the commercially-available stock 20% w/w solution).
$^f$S refers to the sum of polymers listed (X + Z or X + Z + P).
$^g$P = PVP K12 (M$_r$ ~ 1300 daltons).

These observations were helpful, but many problems still required solutions in order to design and demonstrate a successful procedure for both cooling and rewarming whole kidneys with minimization of both chilling injury and any other potentially damaging factors. No one had ever before attempted to determine whether a whole organ could be cooled to a temperature below −10° C. by the perfusion of cold liquid and subsequently recovered in good condition as verified by life support function after transplantation, and specific methods had to be invented. It was not clear that tissue immersion methods for tonicity adjustment and cooling could also be applicable to whole organs whose temperature, tonicity, and cryoprotectant concentration must be controlled by continuous vascular perfusion.

A preferred solution for protecting against chilling injury was, therefore, devised as follows. First, a tonicity of 1.2× was selected for the solution as a tonicity that maximized protection but was also maximally distant from a tonicity of 1.5×. The latter criterion arose from three considerations. First, tonicities in excess of 1.5× (1.5 times isotonic) are hazardous in that they progressively fail to protect against chilling injury as tonicity increases above 1.5× (FIG. 2A). Second, it was considered likely that perfusion with cryoprotectant for a time insufficient for the organ to approach osmotic equilibrium might increase the effective tonicity of the solution. Third, FIG. 2B indicates that renal tissue is able to respond with great rapidity to osmotic transients during cooling. According to FIG. 2B, cooling by transferring slices equilibrated at 1× at 0° C. into a solution having a 2× tonicity at −20° C. is more protective than cooling by transfer into a 1× solution at −20° C. despite the extremely high rate of cooling in these experiments. Generally, a favorable property of a solution to be used for cooling to below −10° C. for the minimization of chilling injury is that the solution be hypertonic.

Second, a specific 1.2× solution was selected by modifying one of the most favorable solutions in Table 1, VM3 (solution 11). VM3 is safe for use on tissue slices at 0° C. (FIG. 1) but is sufficiently concentrated (8.4M) to have a melting point below −22° C. VM3 has a tonicity in 1×LM5 of about 1.7×, but the osmotic contributions of 1% polyvinylalcohol-polyvinylacetate copolymer (PVA) and 1% decaglycerol (PGL) in VM3 sum to about 0.2× (Table 3). VM3 was, therefore, converted into a 1.2 times isotonic test solution for whole kidney perfusion cooling by the expedient of deleting the PVP K12. The new solution was named VMP, for "VM3 Minus PVP." VMP is a fully vitrifiable solution containing a vitrifiable concentration of cryoprotectant, which means that the invention method of diluting cryoprotectant includes a method involving the dilution of a first vitrifiable concentration with a second more dilute but still vitrifiable concentration, without the inclusion of osmotic buffering agents. Similarly, during cryoprotectant addition, the method includes perfusing the organ with a first vitrifiable solution and then with a second, more stable vitrifiable solution. The critical cooling rate of VMP is ≤10° C./min, but its critical warming rate, when this is defined as in FIG. 1, is ~200° C./min, which is too high for use with most organs and tissues that are unable to be warmed at at least 100-200° C./min by conduction or other means. Consequently, the preferred use of VMP in the present invention is as a transitional solution helpful for the introduction and removal of more stable vitrification solutions.

Figure 3A:
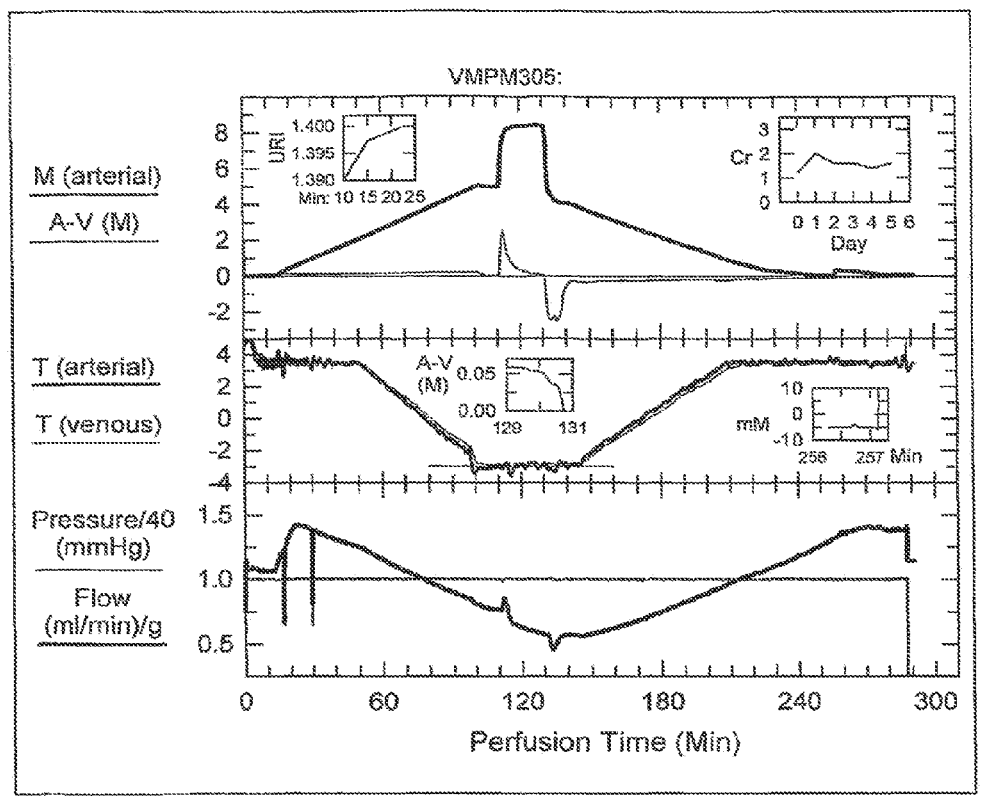
FIG. 3A summarizes a baseline method onto which cooling and warming methods according to the present invention can be superimposed.
Figure 3B:
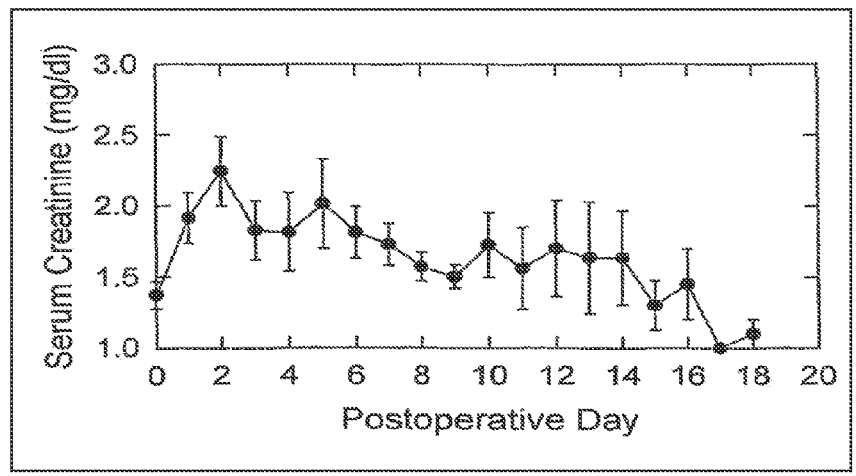
FIG. 3B monitors serum creatinine in seven consecutive transplants following use of the protocol described in FIG. 3A. All transplants resulted in no detectable injury to the kidney, and no use of iloprost, aspirin, or heparin was needed or used.

The next step was to show that VMP would be innocuous when perfused through a whole organ. FIG. 3 describes an effective method for introducing and removing VMP in the rabbit kidney model. This method is typical of methods that are known in the art. However, what was extraordinary, as shown in the inset, was the observation that the VMP solution, which has a total concentration of 8.4M, was completely non-toxic to the rabbit kidney after perfusion for a total of 20 min, which was sufficient for the kidney to approach osmotic equilibrium with the VMP at −3° C. The lack of toxicity of VMP represents a tremendous advance in the art, because the only other 8.4M vitrification solution ever tested on rabbit kidneys, VS55 (also known as VS41A, which is another ~8.4M solution consisting of 3.1M dimethyl sulfoxide, 3.1M formamide, and 2.21M 1,2-propanediol), is absolutely lethal under the same conditions of exposure [1, 17, 21]. In fact, even a solution only ⁵²⁄₅₅ths as concentrated as VS55 is also extremely damaging to the rabbit kidney at −3° C. [19, 20].

Having devised and established the safety of VMP, the next step was to establish methods of actually using VMP to cool whole kidneys by continuous perfusion to about −22° C. This problem, however, could not be studied in the absence of a method for rewarming the kidneys as well. The available art provided no guidance as to whether this degree of cooling and rewarming by continuous vascular perfusion was compatible with subsequent vascular function in vivo or, if potentially compatible, how it should be carried out.

One problem with perfusing an 8.4M solution for 20 min at 0° C. and then following this treatment by perfusion with a solution like M22 is the total amount of time spent with the kidney in contact with concentrations of 8.4M or above. It was attempted, therefore, to deviate from prior art methods by abandoning the requirement that the organ approach osmotic equilibrium with a given solution before it is perfused with the next solution or before cooling commences. However, it was unknown how short a period of perfusion with VMP would be sufficient to prevent the kidney from freezing upon subsequent cooling to about −22° C. Perfusion with VMP was therefore tried according to the protocol given in FIG. 3, but for only 5 or 10 minutes prior to abruptly cooling the arterial perfusate as rapidly as possible by increasing the flow of ~−25° C. coolant over an in-line arterial heat exchanger. Both of these VMP perfusion times are insufficient to allow the kidney to reach approximate osmotic equilibrium with the cryoprotectant. After 10 min of cooling at the maximum rate that could be achieved using a combination of intravascular cooling and cooling of the inner wall of the chamber that contained the kidney, the arterial and venous temperatures approached −22° C. This procedure produced no signs of freezing in the kidney or the arterial perfusate after either 5 or 10 min of VMP perfusion prior to cooling.

Figure 4:
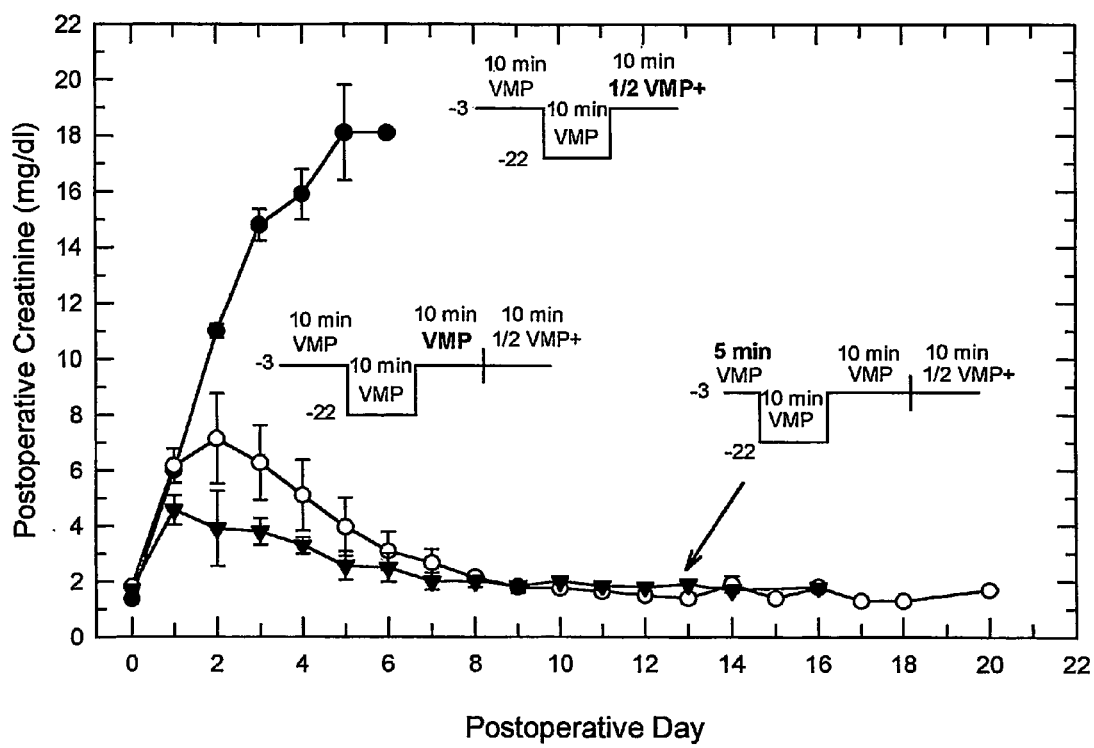
FIG. 4 is a schematic diagram of the programmed continuous perfusion, osmotic non-equilibrium method for minimizing chilling injury and cold dilution damage in whole organs. Rabbit kidneys were perfused with VMP for a nominal 5 or 10 min period at about −3° C. according to FIG. 3 and then for another 10 min while the temperature of the arterial perfusate was set to about −22° C. as rapidly as possible. Each protocol schematic represents the time (horizontal direction) and temperature (vertical direction) of the initial VMP perfusion step at −3° C., the cooling step involving the perfusion of VMP at temperatures down to −22.5±2.5° C., and the subsequent warming and dilution steps. "½ VMP+" refers to half-strength VMP plus 300 mM mannitol as an osmotic buffering agent; 3% HES was also present. The concentration perfused at each step is indicated above the schematic line and the nominal temperature perfused at each step is indicated to the left of each schematic temperature. Bold text in the protocol schematics indicates key differences between the tested protocols. In each case, the preserved kidney served as the sole renal support immediately after transplantation. For each group, n=3. Means±1 standard error of the mean (SEM).

In addition to varying the VMP perfusion time prior to cooling, two different methods were also tried for rewarming the kidneys and removing the VMP. In the first rewarming method, which involved a 10 min VMP perfusion at −3° C. prior to cooling to −22° C., VMP washout was commenced immediately at −3° C., with non-vitrifiable half-strength VMP (a concentration 4.2M less than the concentration perfused at −22° C.) plus the osmotic buffer 300 mM mannitol and the osmotic buffer 3% w/v HES. This method had the advantage of limiting the total time of exposure to VMP to the 20 min previously shown to be safe at −3° C. Nevertheless, 3 consecutive kidneys treated in this way failed to support life after transplantation (FIG. 4).

Suspecting that the cause of the observed injury might be rapid osmotic expansion of brittle tissues near −20° C. as a result of diluting the cryoprotectant prior to the completion of rewarming, the above-described procedure was modified by introducing a 10-min warming step prior to the onset of cryoprotectant washout. This was accomplished using the same warming technique as before, but with no immediate dilution of the VMP during or following rewarming. Although this second method of rewarming exposed the kidney to VMP perfusion for a total of 30 min, all kidneys survived, and post-transplant function was dramatically improved (FIG. 4).

As noted above, the method described relies on cooling without allowing the kidney to reach approximate osmotic equilibrium with VMP prior to cooling. This could be of significance for chilling injury suppression in view of the 1×→2× group of FIG. 2B. If osmotic disequilibrium prior to cooling is important for the results obtained using the second warming method, then modifying the disequilibrium might be able to further improve the protocol. To probe this possibility, and the possibility that some of the injury observed in the continuous perfusion method for cooling and rewarming was due to a long total exposure period to VMP, the period of VMP perfusion was shortened from 10 min to 5 min before cooling to −22° C. This limited the total exposure time to VMP to 25 min and nearly quadrupled osmotic disequilibrium at the onset of cooling as measured by the A-V (arteriovenous) cryoprotectant concentration difference (521±129 after 10 min of perfusion vs. 1967±374 mM for 5 min of perfusion; means±1 standard deviation). This change reduced mean peak creatinine values substantially (FIG. 4). Based on the fact that serum creatinine levels in this group peaked at values similar to those previously obtained with sham-operated control animals [16], it is clear that chilling injury can in fact be suppressed almost entirely at ~−22° C. in whole rabbit kidneys using the final method shown in FIG. 4 and more explicitly in FIG. 5, especially the inset in FIG. 5. The arterial warming rate achieved between −20 and −10° C. in FIG. 5 was 3.15° C./min. Additional details about this procedure and results are described in the figure legend. As demonstrated in later examples, A-V differences of 2.25M just prior to cooling to below −10° C. are also effective in the practice of the present invention. Generally, then, A-V differences higher than 200 mM, and preferably in the range of about 500 to about 2500-3000 mM, are generally desirable just prior to cooling to below −10° C. in the presence of a nominal (at osmotic equilibrium) mildly hypertonic (in this case, 1.2 times isotonic) solution in accordance with the present invention.

Example 3

Method for Perfusing Organs with a Super-Stable Vitrification Solution and Washing it Out Simultaneously with Warming with Minimal Injury The next step was to explore the possibility of perfusing kidneys with M22 in view of its extraordinary stability against ice formation and reasonable toxicity at −22° C. (FIG. 1). However, tissue slice experiments suggested that exposure to M22 at −3° C. would produce unacceptable toxicity, which provisionally ruled out a rewarming procedure like that used for VMP in which it was possible to avoid dilution shock by rewarming prior to dilution.

Figure 6:
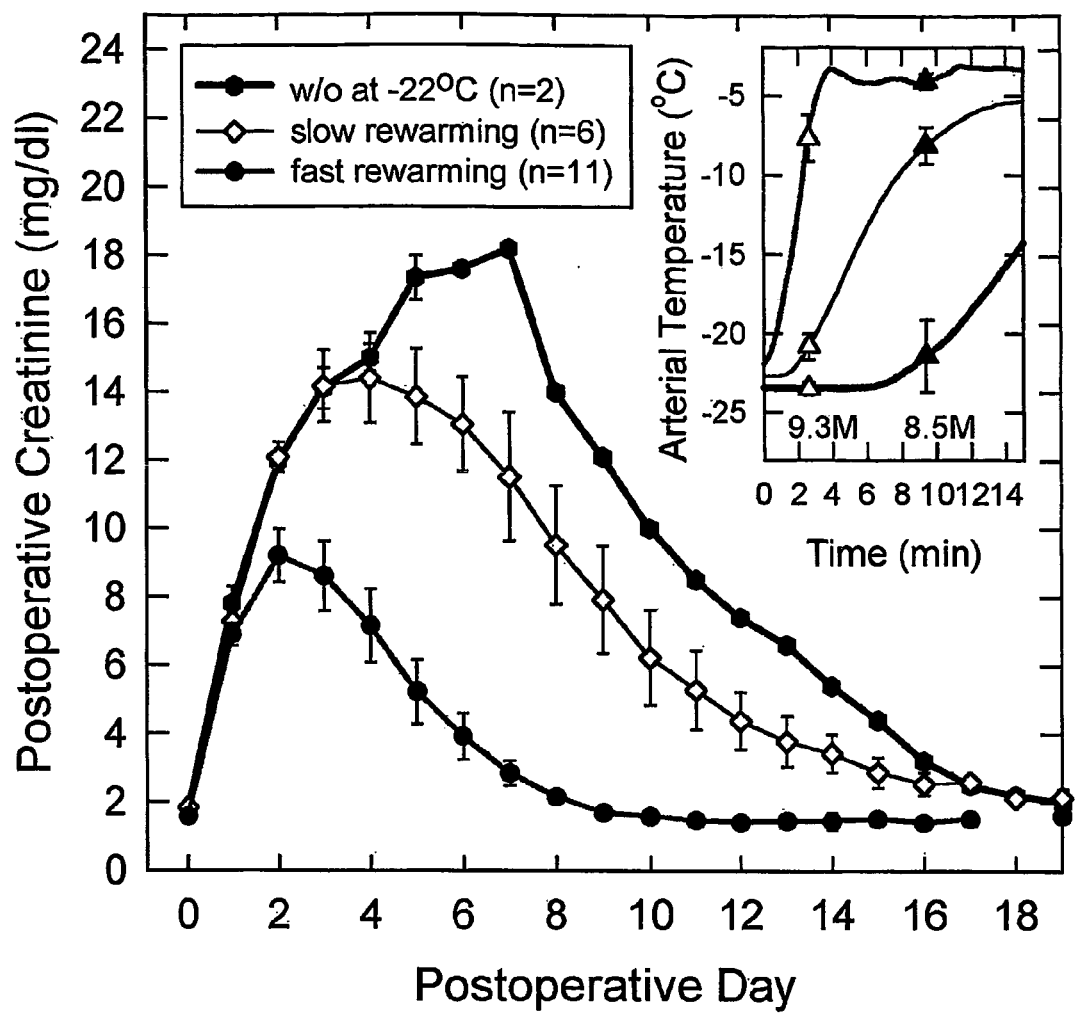
FIG. 6 summarizes results of another exemplary method according to the present invention for continuous perfusion rewarming from below −10° C. with simultaneous dilution of highly vitrifiable concentrations of cryoprotectant and its effect on postoperative creatinine levels. The inset shows three arterial temperature vs. time histories and the times and temperatures at which the measured arterial concentration first began to drop (indicated by the open triangles labeled 9.3M cryoprotectant) and finally began to approach the concentration of VMP (indicated by the filled triangles designating the attainment of 8.5M cryoprotectant). Time zero in the inset represents the time the perfusion machine was set to switch from M22 to VMP; about 2.5 min was required for the programmed switch to result in an actual fall in concentration in these experiments. The line types in the protocol inset match the line types for the same groups in the main panel showing postoperative results. The M22 perfusion time prior to washout at −22° C. was 15-25 min; there was no apparent influence of M22 perfusion time on postoperative creatinine levels (data not shown). Means±1 SEM. The n=11 notation for the rapid-warming, "warm dilution" group pertains to the thermal data in the inset only, with n=8 for the creatinine data for the same group (some kidneys were not transplanted for reasons unrelated to the efficacy of the method described for this group).

Despite the fatality of transitioning from VMP to half-strength VMP+mannitol at −22° C. (50% reduction in molar concentration), the magnitude of the dilution involved in transitioning from M22 to VMP (~10% reduction in molarity) is much smaller. Therefore, it was first considered that this transition might be tolerable at −22° C. despite the evident hazards of osmotic expansion at this temperature. To test this hypothesis, two kidneys were cooled to −22° C. as per the best protocol of FIG. 4, switched to perfusion with M22 at ~−22° C. for 15 min, and then diluted the M22 at −22° C. by perfusion with VMP before perfusing VMP at −3° C. This washout protocol is detailed by the heavy black line in the inset of FIG. 6. One of the two tested kidneys survived, but with a high creatinine peak at 18.2 mg/dl (FIG. 6 main panel, heavy black line).

On the assumption that osmotic expansion damage (i.e., damage caused by increasing cellular and/or interstitial volume due to osmotic ingress of water into these compartments) at temperatures below −10° C. was the main reason for the injury seen in this protocol, the next protocol involved the compromise protocol of simultaneous dilution and warming of the kidney by perfusion with −3° C. VMP for 10 min (middle protocol of FIG. 6). Of 6 kidneys in this group, all survived, and damage appeared to be generally less than with dilution starting at lower temperatures.

These results suggested that osmotic expansion damage at low temperatures was a more important factor than the toxicity of M22 during brief exposure above −22° C. Thus, a powerful heating element was installed in the heat exchange path in order to substantially accelerate the rewarming step, to achieve the final warming protocol shown in FIG. 6 (inset, gray line). The warming rate achieved in this protocol was 9.9±3° C./min between −20° C. and −10° C., as distinguished from the warming rate of 2.3±0.7° C./min (means±1 standard deviation) over the same temperature range in the previous protocol. In both protocols, the rate of cryoprotectant dilution was the same (134±41 mM/min vs. 121±56 mM/min, $p>0.05$; means±1 SD), but the dilution itself occurred at different temperatures in the two groups because warming began immediately whereas the concentration response lagged by about 2.5 min, allowing warming to precede dilution more and more as the warming rate increased. The result of the accelerated warming treatment was that the kidneys were briefly exposed to M22 perfusion at temperatures generally above −10° C. prior to experiencing dilution by VMP, and this produced a dramatic improvement in recovery after 15, 20, or even 25 min of previous M22 perfusion, with no increase in injury with increasing M22 perfusion time over this range (data not shown).

Figure 7:
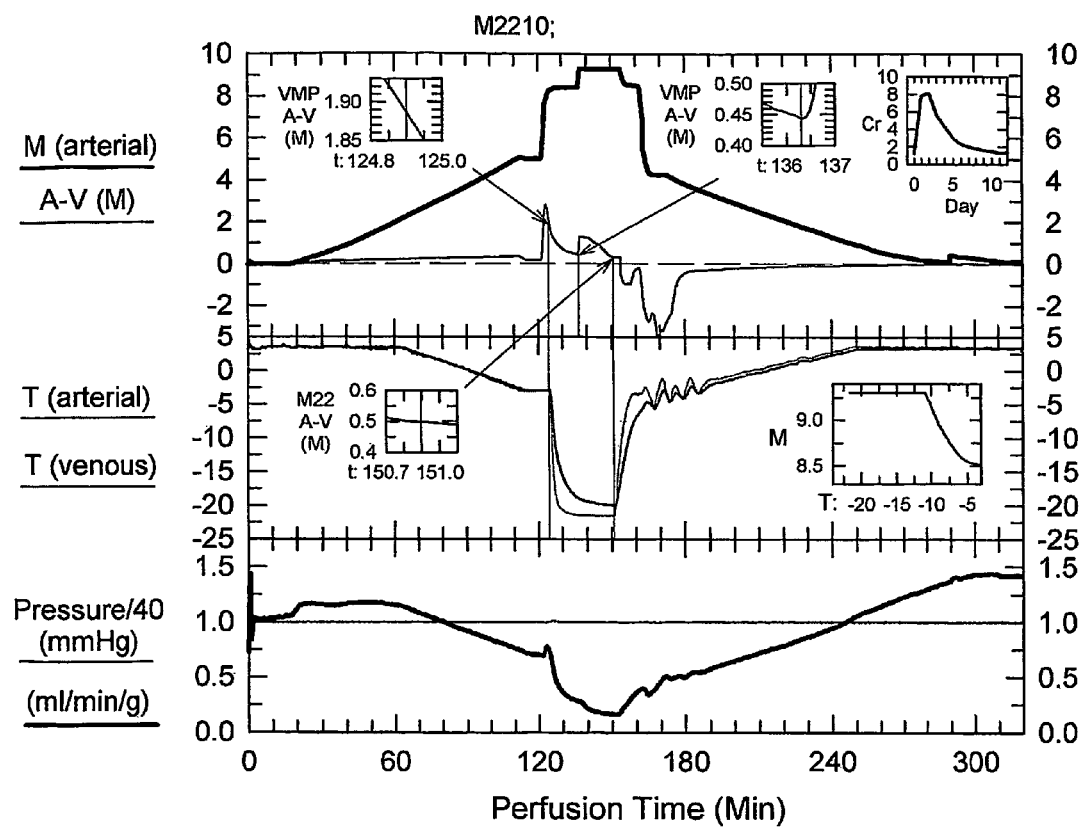
FIG. 7 summarizes results with another exemplary protocol according to the present invention for the successful recovery of organs after perfusion with vitrifiable concentrations of cryoprotectant below −10° C. using the simultaneous rewarming and dilution method of FIG. 6. The same format and abbreviations are employed herein as in FIGS. 3 and 5. Insets show lack of approximate osmotic equilibrium at onset of cooling (upper left inset), lack of approximate osmotic equilibrium at onset of perfusion with the final vitrification solution (upper middle inset), lack of approximate osmotic equilibrium at the time of onset of warming, which is the nominal time to cool and vitrify the organ (middle left inset), the relationship between arterial molarity and temperature during perfusion-rewarming (middle right inset), and postoperative serum creatinine levels (upper right inset). The temperature control instabilities shown immediately after rapid warming from −22° C. were not typical of this protocol, but illustrate the tolerance of the organ to mild temperature fluctuations within this range.

The overall best 25 min M22 perfusion protocol resulting from these experiments is illustrated in FIG. 7 and further discussed in the FIG. 7 legend. Note that FIG. 7 demonstrates a clear and obvious lack of approximate osmotic equilibrium of the organ with the perfusate at each key transition point in the process, as expanded upon in the insets. FIG. 7 also contains an inset in which arterial molarity is plotted against arterial temperature. This inset shows that the arterial molarity began to drop slightly just before the temperature rose to −10° C. The kidney recovered very well, however, indicating that although dilution above −10° C. is desirable in the best mode of the invention, slight dilution between −15° C. and −10° C. is also fully consistent with the successful practice of the invention, and the ideal dilution temperature of −10° C. and above is not an absolute requirement of the invention. However, the dilution below −10° C. in this inset is small and the dilution nominally if not literally is indeed above −10° C., and is literally above −10° C. for the vast majority of the dilution.

Example 4

Methods for Successfully Cooling Organs to and Warming Organs from Temperatures Below ~−22° C.

Figure 8:
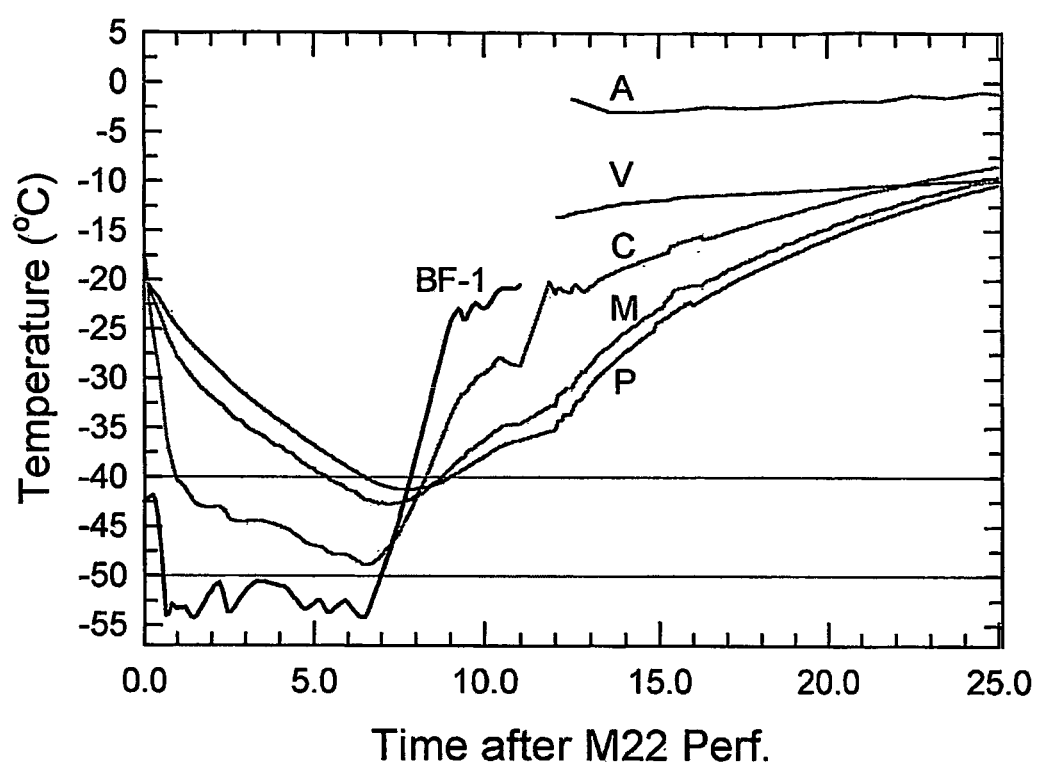
FIG. 8 presents the environmental and intrarenal thermal history of a rabbit kidney exposed to −50° C. by forced convection for 6 min and then rewarmed. C=cortical temperature (2 mm below the renal surface); M=medullary temperature (7 mm below the renal surface); P=papillary/pelvic temperature (12 mm below the renal surface); BF1=temperature of rapidly-moving air in contact with the renal surface in a Linde BF-1 Biological Freezer; A=arterial temperature during reperfusion, V=venous temperature during reperfusion. Intra-renal temperatures were monitored using a PhysiTemp (Huron, Pa.) triple bead needle probe. Horizontal lines illustrate that all parts of the kidney were between −40° C. and −50° C. at the time of onset of warming. Reperfusion for rewarming was accomplished using Method 1 described in conjunction with FIG. 9.

In order to develop procedures for cooling kidneys removed from the perfusion machine and to probe the impact of chilling injury below −22° C., several M22-perfused kidneys were placed in a −50° C. environment for 6 min and then rewarmed in air for 4 min, then reperfused for M22 washout according to the method described above, with the perfusate starting at −22° C. and rising rapidly. Cooling was accomplished using a Linde BF1 air cooling unit in which liquid nitrogen was injected into a vigorously circulated air chamber as needed to attain the desired temperatures. Upon warming, dry ambient temperature nitrogen was bled into the chamber to maintain a positive pressure in the unit and therefore avoid the formation of frost from the entry of ambient air into the cold chamber. The total time spent from removal of the kidney from the perfusion machine to the beginning of reperfusion was about 11 min. FIG. 8 shows an example of the cooling and warming procedure used in these experiments and the resulting thermal profiles within one sample kidney obtained using a three-junction needle thermocouple inserted directly into the kidney. The direct intrarenal temperature measurements were in agreement with expectation and confirmed that all parts of the kidney were at least as cold as −40 to −50° C. at the end of cooling. Presumably, the more superficial cortex approached the environmental temperature of −50 to −55° C. Due to electrical interference, the transition from −22° C. to −3° C. was not correctly documented by the vascular probes in this experiment, and erroneous data are omitted from the plot for these probes.

Figure 9:
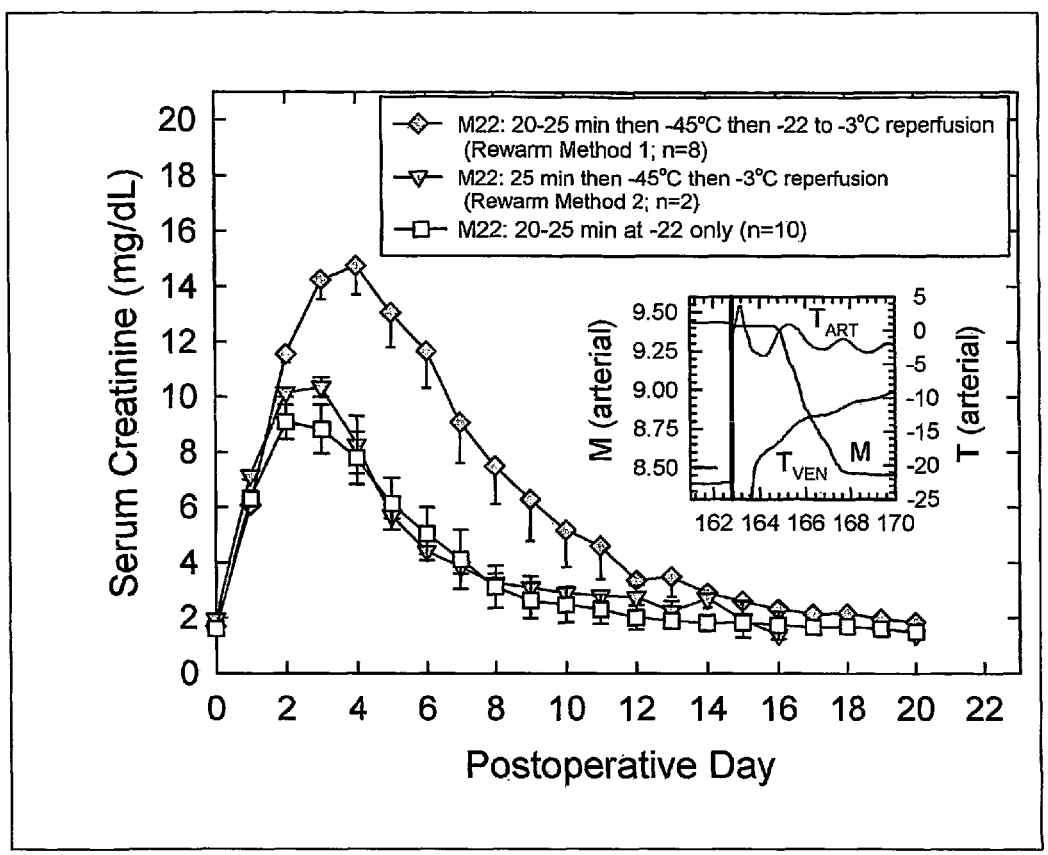
FIG. 9 illustrates the effects of two exemplary methods according to the present invention for the prevention of damage after cooling an organ to −45° C. Rewarm Method 1 (diamonds) employed the M22 washout method described with reference to FIGS. 6 and 7. In this method, M22 in the arterial perfusion line was held at −22° C. until the cooled organ was reattached to the perfusion machine and reperfused, after which rapid warming of the arterial perfusate proceeded as in FIGS. 6 and 7. In Rewarm Method 2 (inverted triangles), the perfusate temperature was increased to −3° C. during the time the organ was not perfused. When the organ was reattached to the perfusion machine, it was reperfused directly with vitrifiable concentrations of cryoprotectant at −3° C. for a total of 2.4±0.7 min before beginning to experience dilution of the arterial perfusate. The inset shows a vertical line marking the discontinuity in perfusion required for cooling to and rewarming from about −45° C.; except for calibration drift in the arterial refractometer, there is no change in arterial concentration but there is a step change in temperature when the organ is reperfused after having previously been cooled to −45° C. At the time of onset of reduction in arterial concentration, venous temperature is around −17° C. despite the more rapid warming in Method 2, but rises to above −10° C. in less than 10 min, suggesting that 10 min of −3° C. perfusion will be sufficient to return all parts of an organ to a temperature at which dilution to lower concentrations is safe. The Method 1 −45° C. group was perfused with M22 at ~−22° C. (arterial temperature, −22.5±2.5° C.) for 20 (n=2) or 25 (n=6) min before further cooling and rewarming as in FIG. 7. The Method 2 −45° C. group was perfused with "M22MX", which consists of M22 lacking "X1000" (a copolymer of polyvinyl alcohol and polyvinyl acetate described in detail elsewhere), for 25 min as in Method 1, cooled to −45° C. as in Method 1, and reperfused at −3° C. with M22MX after prior external warming to a surface temperature of about −22°. Means±1 SEM.

FIG. 9 compares the damage done by cooling to below −40° C. and warming using two different methods to the effects of simply perfusing M22. In the first −45° C. protocol, rabbit kidneys cooled to −45±5° C. were rewarmed in air to a surface temperature near −20° C., then attached to the perfusion machine and perfused with M22 starting at about −22° C. and proceeding as shown in FIG. 6. This resulted in the recovery of all kidneys so treated (8/8), but postoperative creatinine levels were elevated. However, deep intrarenal temperatures at the onset of reperfusion with VMP approximated −35° C. (FIG. 8), which could put these areas at additional risk of brittle tissue osmotic expansion (dilution) damage.

In an effort to further reduce putative brittle tissue osmotic expansion injury (dilution shock), a radical second method of rewarming kidneys from temperatures below −15° C. was tested. For reasons unrelated to the nature of this test, these experiments were carried out using a variation of M22 called M22MX (for "M22 Minus X-1000"). M22MX is M22 from which PVA (or more precisely, a copolymer of polyvinyl alcohol and polyvinyl acetate made by hydrolyzing 80% of the acetate moieties of polyvinyl acetate to alcohol groups, a commercially available product called "Supercool X-1000") was omitted. In the new method, the M22MX perfusate was not gradually rewarmed from −22° C. during continuous organ perfusion, but was reset to a temperature of −3° C. while the kidney was disconnected from the perfusion machine and was being cooled to −45° C. After 4 min of rewarming in air as before, the kidney was directly perfused with M22MX at about −3° C. or above to rapidly rewarm the renal core for about 2-3 min, after which the perfusate began to revert to VMP as usual (see inset of FIG. 9). The total time during which M22MX at about −3° C. or above was perfused before the onset of dilution to VMP was 2.38±0.69 min (mean±1 standard deviation). The surprisingly sweeping result of this process modification, as shown in FIG. 9, was the complete abolition of all apparent chilling injury below −22° C.

Following the venous temperature of the example kidney shown in the FIG. 9 inset, it can be seen that the venous temperature remained below −10° C. for ~6-7 min. This observation suggests that for most organs, "warm" perfusion with vitrifiable media need not continue for longer than 10 min to restore internal structures to a safe temperature for dilution. Generally, therefore, 1-10 min of "warm" (nominally ≥10° C.) perfusion should be sufficient.

The relatively extreme fluctuations of arterial temperature shown in the inset were not typical of the final method, but show that the kidney can be briefly perfused with a super-vitrifiable and super-stable vitrification solution at temperatures as high as about 0° C. to +5° C. with subsequent excellent renal recovery even after prior cooling to an average internal temperature of about −45° C.

Example 5

Optimizing Perfusion Pressure in the Organ Cryopreservation Protocol

Figure 10:
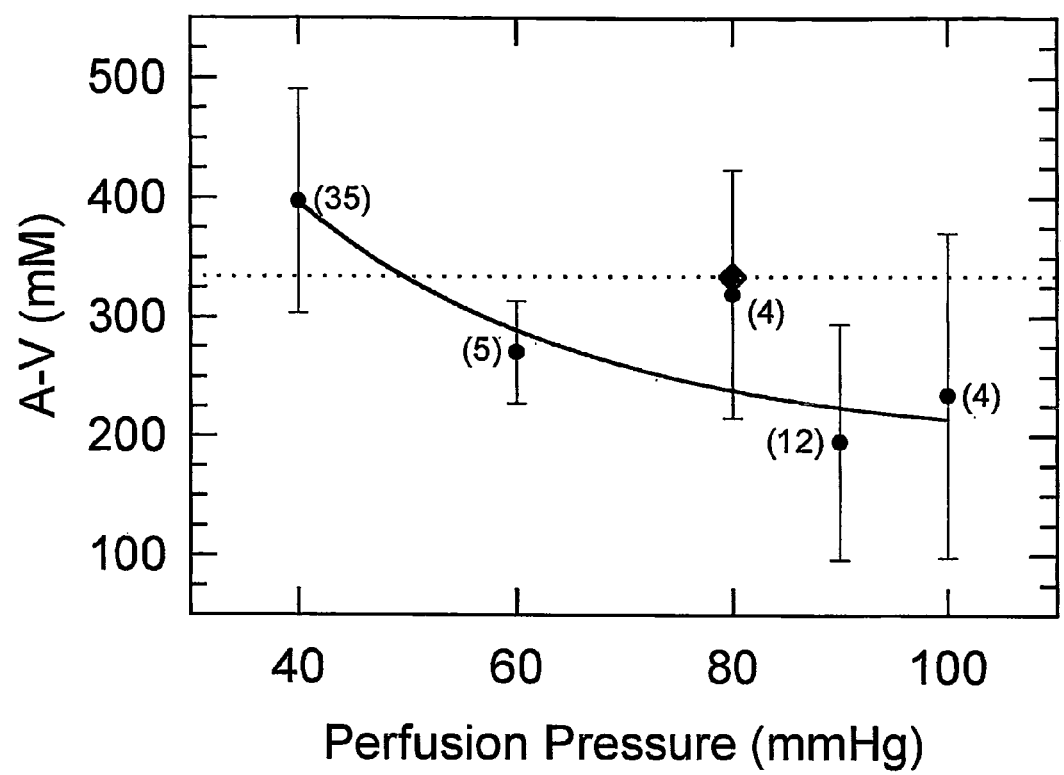
FIG. 10 is a graph of the effect of arterial perfusion pressure during M22 perfusion on tissue equilibration with cryoprotectant as measured by arteriovenous (A-V) concentration difference. In all cases, A-V differences were measured at the end of 25 minutes of perfusion with M22, the arterial perfusion pressure was 40 mmHg prior to perfusion with M22, and pressure was set to the value plotted at the time of onset of M22 perfusion. The A-V difference is the arterial perfusate concentration minus the organ effluent concentration (venous concentration).

Traditionally, perfusion pressures of greater than 40 mmHg have been considered highly hazardous, and during the perfusion of vitrifiable concentrations of cryoprotectant, perfusion pressures of 30 mmHg have been favored in view of the vascular damage caused by previously available vitrification solutions. Nevertheless, results such as those shown above suggested that pressures above 40 mmHg might be tolerated using M22 as the vitrification solution due to the extraordinary lack of toxicity of this solution when used within the process limits of the invention. Elevating perfusion pressure was therefore evaluated for its effect on the arterio-venous (A-V) concentration difference at the end of M22 perfusion. In accordance with the present invention, it was found that elevating perfusion pressure to 60 mmHg reduced the A-V concentration difference almost as much as increasing it to 90 or 100 mmHg, and no improvement was apparent at 80 mmHg compared to 60 mmHg (FIG. 10). Furthermore, when kidneys were perfused at 40, 60, or 100 mmHg, tissue stability, as measured by the amount of ice that formed in the inner medulla after vitrification and rewarming, by the glass transition temperature of the tissue, and by the melting point of the tissue, were all better at 60 mmHg than at either 40 mmHg or 100 mmHg in a limited number of observations (Table 4). Further, the standard deviation of the A-V differences at 60 mmHg was smaller than the standard deviations at either lower or higher pressures (FIG. 10). Therefore, although the very best (lowest) A-V differences were seen at 90 and 100 mmHg, the fact that the improvement was not consistent suggests the possibility of vascular damage leading to impaired tissue distribution of cryoprotectant in some kidneys. However, there was no clear trend for postoperative serum creatinine levels to rise with increasing perfusion pressure within the limited number of observations made, so perfusion pressures of up to 100 mmHg for small organs and 110-120 mmHg for large organs may be acceptable. Nevertheless, the graph of FIG. 10 suggests that the optimum combination of efficacy and safety is obtainable using pressures of 50-90 mmHg or more preferably 55-85 mmHg, or still more preferably 60-80 mmHg for small organs (<=50 grams in weight). For large organs (>50 grams in weight), the most preferred range is 50-90 mmHg, and optimal pressures will generally be 10-20 mmHg higher than for smaller organs.

FIG. 10 indicates that 60 mmHg is sufficient also with respect to another important criterion. FIG. 10 shows a point plotted at 80 mmHg and an A-V difference of 334 mM. This A-V difference (dotted line) has particular significance because it is the A-V difference of a kidney that was able to permanently support the life of a recipient rabbit after vitrification, rewarming, M22 washout, and transplantation, as described in more detail in Example 6. As can be seen from FIG. 10, a perfusion pressure of 60 mmHg will generally achieve an A-V difference at least as low as was necessary to retain life support function after vitrification and rewarming. Although failure to attain approximate osmotic equilibrium between the organ and the perfusate is advantageous prior to cooling to below −10° C. and prior to the onset of perfusion with the final vitrification solution such as M22, failure to attain approximate osmotic equilibrium with the final vitrification solution should not be unnecessarily increased even though it is compatible with survival after vitrification and rewarming, because it results in less stability against ice formation in the organ. Therefore, a proper balance must be reached between stabilizing the organ and avoiding excessive exposure to the final vitrification solution. For M22, an A-V difference between 200 and 300 mM, and even of 100-300 mM, is desirable for good stabilization of kidneys against ice formation.

The survival of a vitrified-rewarmed kidney after perfusion with M22 at 80 mmHg as shown in Example 6 below also clearly demonstrates that 80 mmHg is efficacious in the invention.

TABLE 4

Effect of Perfusion Pressure on Inner Medulla Stability Against Freezing and Tissue Cryoprotectant Concentrations After M22 Perfusion[a]

| Pressure | Tissue $\Delta H_M$ | Tissue $T_g$ | Tissue $T_m$ | Tissue M22 (% w/v) | Tissue % Equilibration | Venous % Equilibration | 100% × $C_T$/$C_V$ |
|---|---|---|---|---|---|---|---|
| 40 | 5.3 | −121.6 | −42.9 | 58.85 | 90.8 | 97.9 | 92.7 |
| 60 | 2.8 | −120.3 | −45.9 | 60.7 | 93.7 | 96.7 | 96.9 |
| 100 | 4.3 | −121.6 | −41.6 | 58.0 | 89.5 | 95.9 | 93.3 |

[a]Explanation of column headings:
pressure = arterial pressure, in mmHg;
tissue $\Delta H_M$ = heat (in joules/gram) required to melt all ice that previously formed in the tissue sample during both cooling and warming as measured at a warming rate of 20° C./min;
tissue $T_g$ = tissue glass transition temperature measured at a warming rate of 20° C./min;
tissue $T_m$ = tissue melting point measured during warming at 20° C./min;
tissue M22 = apparent tissue concentration of M22 solutes, in % w/v units, derived as described below and in the text;
tissue % equilibration = 100% × (tissue M22)/64.8, where 64.8 is the total concentration of M22 in % w/v units;
venous % equilibration = apparent venous (effluent) concentration of M22 solutes, expressed as a percentage of the concentration of M22;
100% × $C_T$/$C_V$ = the apparent tissue cryoprotectant concentration ($C_T$) expressed as a percent of the apparent venous cryoprotectant concentration ($C_V$).
Tissue $T_m$ values were converted to apparent tissue concentrations by reading the value of % w/v M22 solutes having the same $T_m$ as the tissue $T_m$ on a graph of $T_m$ vs the concentration of dilutions of M22 in LM5 (no calcium, no magnesium). These dilutions were made by diluting M22 prepared in LM5 (no calcium, no magnesium) with LM5 (no calcium, no magnesium).

Example 6

Figure 11:
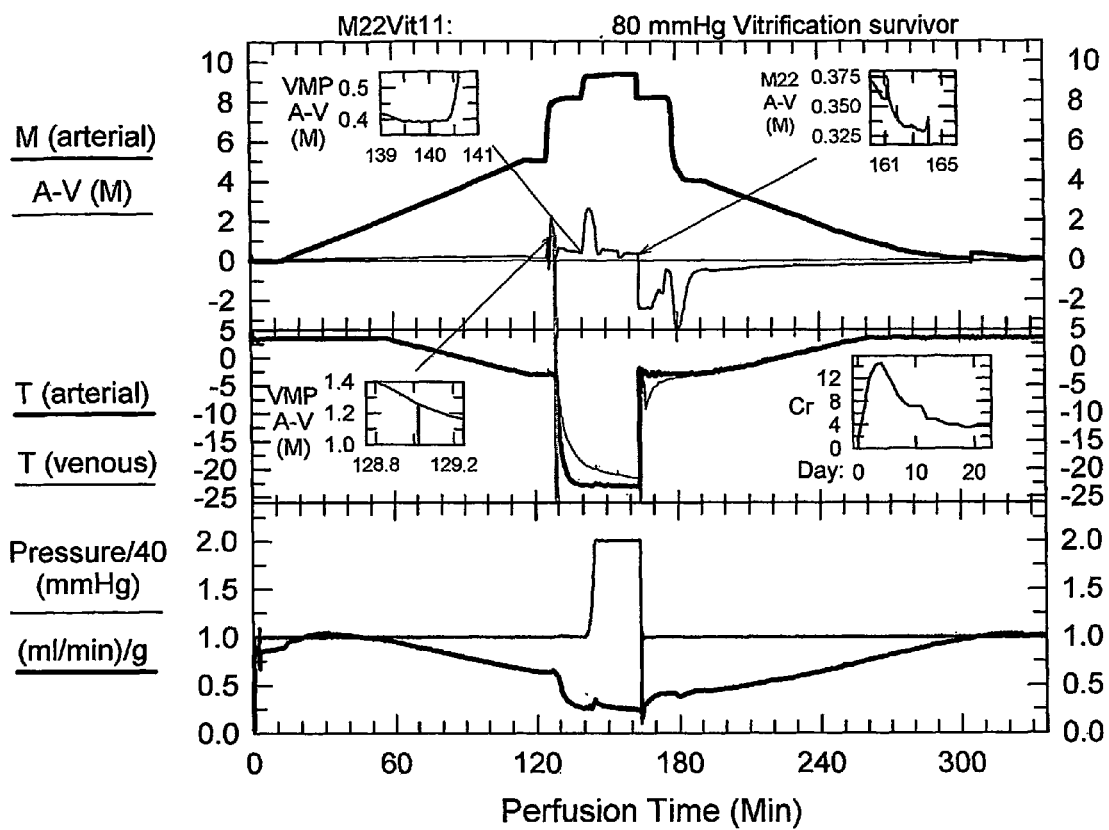
FIG. 11 summarizes the perfusion record and postoperative recovery data for a rabbit kidney that was perfused with M22, vitrified, rewarmed, transplanted, and supported life as the sole kidney until the recipient was euthanized 40 days after transplantation.

Survival of, and Life Support by, a Vitrified, Rewarmed, Transplanted Rabbit Kidney with Immediate Contralateral Nephrectomy A rabbit kidney was perfused according to the protocol shown in FIG. 11. The A-V difference upon cooling (middle left inset) was about 1.25M, and was about 0.4M upon transitioning to M22 (upper left inset), both representing large departures from approximate osmotic equilibrium. At the end of M22 perfusion, when the kidney was removed from the perfusion machine and actually vitrified (the intervening time being edited out of the perfusion record as usual to show the complete perfusion record without displaying the perfusion interruption), the A-V difference was 334 mM (upper right inset). The kidney was cooled to below the glass transition temperature of M22 (about −122 to −124° C.), rewarmed, and reperfused at −3° C. with the vitrifiable VMP solution lacking any osmotic buffering agents. The venous temperature approached the arterial temperature within about 15 min. This kidney yielded a peak creatinine level of 14.6 mg/dl. This kidney was perfused at 80 mmHg during the M22 phase only (bottom panel). In this experiment, the organ was warmed externally to a temperature higher than a temperature which permits the organ to be perfused and was perfused with a reduced but still vitrifiable concentration of cryoprotectant (VMP) that did not contain an osmotic buffering agent. Note that as commonly understood in the art, an osmotic buffering agent must be an agent newly present in or increased in concentration in a diluent in order to buffer or at least partly offset the osmotic effect of reducing the concentration of permeating (≤150 dalton) cryoprotectant in the same diluent. An osmotic buffer is used to raise the total osmolality of the diluent other than the osmotic contribution of the ≤150 dalton (nominally permeating) cryoprotectants in the diluent, to buffer the fact of the reduction of the total osmolality of those permeating cryoprotectants. No chemical is present in VMP that is not present in M22, or present in a higher concentration in VMP than in M22, or used to increase the osmolality of the components of VMP other than its permeating cryoprotectants in comparison to the osmolality of the components of M22 other than its permeating cryoprotectants. Therefore, it is clear that VMP does not contain even one osmotic buffering agent.

While the invention has been described in detail with reference to certain preferred embodiments thereof, it will be understood that modifications and variations are within the spirit and scope of that which is described and claimed.

REFERENCES

1. Arnaud, F. G., B. Khirabadi and G. M. Fahy, *Physiological evaluation of a rabbit kidney perfused with VS41A*. Cryobiology, 2003. 46: p. 289-294.
2. Fahy, G. M., *Analysis of "solution effects" injury: cooling rate dependence of the functional and morphological sequellae of freezing in rabbit renal cortex protected with dimethyl sulfoxide*. Cryobiology, 1981. 18: p. 550-570.
3. Fahy, G. M., *Prospects for vitrification of whole organs*. Cryobiology, 1981. 18: p. 617.
4. Fahy, G. M., *Cryoprotectant toxicity: biochemical or osmotic?* Cryo-Letters, 1984. 5: p. 79-90.
5. Fahy, G. M., An advantageous carrier solution for vitrifiable concentrations of cryoprotectants, and compatible cryoprotectant mixtures. 2001: U.S. patent application Ser. No. 09/916,396.
6. Fahy, G. M. and B. Wowk, Cryoprotectant solution containing dimethyl sulfoxide, an amide and ethylene glycol, in May 28, 2002: U.S. Pat. No. 6,395,467 B1.
7. Fahy, G. M. and J. Wu, Polyglycerol and lactose compositions for the protection of living systems from states of reduced metabolism, in PCT; Aug. 14, 2003: International patent number WO 03/065801 A2.
8. Fahy, G. M., D. I. Levy and S. E. Ali, *Some emerging principles underlying the physical properties, biological actions, and utility of vitrification solutions*. Cryobiology, 1987. 24: p. 196-213.
9. Fahy, G. M., D. R. MacFarlane, C. A. Angell and H. T. Meryman, *Vitrification as an approach to cryopreservation*. Cryobiology, 1984. 21: p. 407-426.
10. Fahy, G. M., B. Wowk, J. Wu and S. Paynter, *Improved vitrification solutions based on predictability of vitrification solution toxicity*. Cryobiology, 2004. 48: p. 22-35.
11. Fahy, G. M., C. da Mouta, L. Tsonev, B. S. Khirabadi, P. Mehl, and H. T. Meryman, *Cellular injury associated with organ cryopreservation: chemical toxicity and cooling injury*, in *Cell Biology of Trauma*, J. J. Lemasters and C. Oliver, Editors. 1995, CRC Press: Boca Raton.
12. Jacobsen, I. A., D. E. Pegg, H. Starklint, C. J. Hunt, P. Barfort, and M. P. Diaper, *introduction and removal of cryoprotective agents with rabbit kidneys: assessment by transplantation*. Cryobiology, 1988. 25: p. 285-299.
13. Karlsson, J. O. and M. Toner, *Cryopreservation*, in *Principles of Tissue Engineering, Second Edition*, R. P. Lanza, R. Langer, and J. Vacanti, Editors. 2000, Academic Press: San Diego. p. 293-307.
14. Karow, A. M., Jr, *The organ bank concept*, in *Organ Preservation for Transplantation*, A. M. Karow, Jr, G. J. M. Abouna, and A. L. Humphries, Jr, Editors. 1974, Little, Brown and Company: Boston. p. 3-8.
15. Khirabadi, B. and G. M. Fahy, *Permanent life support by kidneys perfused with a vitrifiable (7.5 molar) cryoprotectant solution*. Transplantation, 2000. 70(1): p. 51-57.
16. Khirabadi, B. S. and G. M. Fahy, *Cryopreservation of the mammalian kidney. I. Transplantation of rabbit kidneys perfused with EC and RPS-2 at 2-4° C.* Cryobiology, 1994. 31: p. 10-25.
17. Khirabadi, B. S., G. M. Fahy and L. S. Ewing, *Survival of rabbit kidneys perfused with 8.4 M cryoprotectant*. Cryobiology, 1995. 32: p. 543-544.
18. Khirabadi, B. S., F. Arnaud and E. Kapnik, *The effect of vitrification on viability of rabbit renal tissue*. Cryobiology, 1998. 37: p. 447.
19. Khirabadi, B. S., G. M. Fahy, J. Saur and H. T. Meryman, *Perfusion of rabbit kidneys with 8 molar cryoprotectant (V52)*. Cryobiology, 1993. 30: p. 611-612.
20. Khirabadi, B. S., G. M. Fahy, P. Nannini, J. Saur and H. T. Meryman, *Life support function of rabbit kidneys perfused with 8 molar cryoprotectant*. Cryobiology, 1993. 30: p. 612.
21. Khirabadi, B. S., G. M. Fahy, J. Saur, L. Ewing and H. T. Meryman, *Failure of rabbit kidneys to survive chilling to −30° C. after perfusion with 8 M cryoprotectant at −3° C.* Cryobiology, 1994. 31: p. 596-597.
22. Khirabadi, B. S., G. M. Fahy, L. Ewing, J. Saur and H. T. Meryman, *100% survival of rabbit kidneys chilled to −32° C. after perfusion with 8 M cryoprotectant at −22° C.* Cryobiology, 1994. 31: p. 597.
23. Lysaght, M. J., N. A. Nguy and K. Sullivan, *An economic survey of the emerging tissue engineering industry*. Tissue Engineering, 1998. 4(3): p. 231-238.
24. Pegg, D. E., *Banking of cells, tissues, and organs at low temperatures*, in *Current Trends in Cryobiology*, A. U. Smith, Editor. 1970, Plenum Press: New York. p. 153-180.
25. Pegg, D. E., *Theory and experiments towards subzero organ preservation*, in *Organ Preservation*, D. E. Pegg, Editor. 1973, Churchill Livingstone: London. p. 108-122.
26. Pegg, D. E. and M. P. Diaper, *The mechanism of cryoinjury in glycerol-treated rabbit kidneys*, in *Organ Preservation, Basic and Applied Aspects*, D. E. Pegg, I. A. Jacobsen, and N. A. Halasz, Editors. 1982, MTP Press, Ltd: Lancaster. p. 389-393.

27. Rail, W. F. and G. M. Fahy, *Ice-free cryopreservation of mouse embryos at −196° C. by vitrification.* Nature, 1985. 313: p. 573-575.
28. Starzl, T. E., *A look ahead at transplantation.* Journal of surgical research, 1970. 10: p. 291-297.
29. Wang, X., H. Chen, H. Yin, S. Kim, S. Lin Tan, and R. Gosden, *Fertility after intact ovary transplantation.* Nature, 2002. 415(385).

That which is claimed is:

1. A method for cooling an organ from a temperature above −10° C. to a target temperature below −10° C. by continuous vascular perfusion with minimal injury, said method comprising:
   perfusing the organ with a vitrifiable first cryoprotectant solution having a first cryoprotectant concentration, wherein said perfusing is conducted for a period of time insufficient for the difference between the first cryoprotectant concentration and the venous cryoprotectant concentration of said organ to decline to 200 mM or less; and then, at the end of said period of time,
   lowering the temperature of the first cryoprotectant solution to or below the target temperature while continuously perfusing the organ; and thereafter
   continuing to perfuse said first cryoprotectant solution until the temperature of at least a portion of the organ reaches the target temperature,
   wherein the first cryoprotectant solution is sufficiently concentrated to be vitrifiable at a cooling rate of ≤20° C./min.

2. The method of claim 1 wherein the first cryoprotectant solution comprises 22.3% dimethyl sulfoxide (DMSO), 12.9% formamide, 16.8% ethylene glycol, 1% polyglycerol, and 1% polyvinyl alcohol or a copolymer of polyvinyl alcohol and polyvinyl acetate, all concentrations being weight/volume percentages.

3. The method of claim 1 wherein the first cryoprotectant solution is hypertonic.

4. The method of claim 1, wherein the first cryoprotectant solution has an equilibrium tonicity in the range of about 1.1 to about 1.6 times isotonic.

5. The method of claim 1 wherein the concentration of the first cryoprotectant solution is 500-3,000 mM higher than the venous concentration at the time cooling to below −10° C. begins.

6. The method of claim 1, wherein the step of perfusing the organ with a first cryoprotectant solution is accomplished by replacing an organ preservation solution initially present in the organ with the first cryoprotectant solution containing a carrier solution component that is different from the initial organ preservation solution.

7. The method of claim 1 wherein the arterial perfusion pressure is about 40-110 mmHg.

8. The method of claim 7 wherein the arterial perfusion pressure is about 50-90 mmHg.

9. The method of claim 7 wherein the arterial perfusion pressure is about 55-85 mmHg.

10. The method of claim 1 wherein the arterial perfusion pressure is 40±8 mmHg before cooling begins.

11. The method of claim 10 wherein the arterial perfusion pressure is elevated to 41-110 mmHg as cooling begins.

12. The method of claim 1 wherein the target temperature is −15° C. or below.

13. The method of claim 1 wherein the target temperature is above −40° C.

14. The method of claim 1 wherein the target temperature is −20 to −30° C.

15. The method of claim 1 further comprising, after at least a portion of the organ reaches the target temperature, perfusing the organ with a second cryoprotectant solution capable of allowing the organ to vitrify if the organ is subsequently cooled at ≤20° C./min, said second cryoprotectant solution being at the target temperature.

16. The method of claim 15 wherein said second cryoprotectant solution capable of allowing the organ to vitrify comprises:
   20.9%-24.2% DMSO,
   12.49-17.2% formamide,
   15.3-23.84% ethylene glycol,
   0-7% acetol,
   0-7% polyvinyl pyrrolidone K30,
   0-8% polyvinyl pyrrolidone K12,
   0-4% polyglycerol,
   0-1% polyvinyl alcohol or a copolymer of polyvinyl alcohol and polyvinyl acetate,
   0-3% N-methylformamide, and
   0-4% 3-methoxy-1,2-propanediol, all concentrations being weight/volume percentages.

17. The method of claim 15, wherein said second cryoprotectant solution capable of allowing the organ to vitrify comprises dimethyl sulfoxide, ethylene glycol, polyglycerol, polyvinyl alcohol or a polyvinyl alcohol-polyvinyl acetate copolymer, polyvinyl pyrrolidone, formamide, N-methylformamide, and 3 methoxy-1,2-propanediol.

18. The method of claim 17, wherein said second cryoprotectant solution capable of allowing the organ to vitrify comprises dimethyl sulfoxide, ethylene glycol, polyglycerol, polyvinyl alcohol or a polyvinyl alcohol-polyvinyl acetate copolymer, low molecular mass polyvinyl pyrrolidone, formamide, N-methylformamide, and 3-methoxy-1,2-propanediol, wherein the solution is sufficiently concentrated to remain ice-free based on differential scanning calorimetry when vitrified and then rewarmed at less than 1° C./min.

19. The method of claim 17, wherein said second cryoprotectant solution capable of allowing the organ to vitrify comprises:

| | |
|---|---|
| Dimethyl sulfoxide | 2.855 M (22.305% w/v) |
| Formamide | 2.855 M (12.858% w/v) |
| Ethylene glycol | 2.713 M (16.837% w/v) |
| N-methylformamide | 0.508 M (3% w/v) |
| 3-methoxy,1,2-propanediol | 0.377 M (4% w/v) |
| Polyvinylpyrrolidone (PVP) K12 | 2.8% w/v (~0.0056 M) |
| Polyvinyl alcohol (PVA)[a] | 1% w/v[b] (~0.005 M) |
| Polyglycerol (PGL) | 2% w/v[b] (~0.0267 M) |
| Total cryoprotectant concentration | 9.345 M (64.8% w/v) |
| pH | 8.0 |
| Nominal tonicity | 1.5 times isotonic |
| Melting point | ~−54.9° C. (estimated) |
| Critical warming rate | <1° C./min. |

[a]PVA comprises a polyvinylalcohol-polyvinylacetate copolymer in which approximately 80% of the alcohol or acetate moieties are hydroxyl groups and 20% are acetyl groups;
[b]Final polymer concentrations.

20. The method of claim 17, wherein said second cryoprotectant solution further comprises polyethylene glycol.

21. The method of claim 20, wherein the polyethylene glycol has a mean molecular mass of about 600 to 4000 daltons.

22. The method of claim 17, wherein said second cryoprotectant solution has a total concentration of about 9.3 molar or about 64.8% weight/volume.

23. The method of claim 15, further comprising interrupting perfusion after perfusing with the second cryoprotectant solution, and cooling the organ to a temperature below the target temperature.

24. The method of claim 15, further comprising:
  interrupting perfusion after perfusing with the second cryoprotectant solution;
  cooling the organ to a temperature below the target temperature while perfusion of the organ remains interrupted; and
  rewarming the organ to a temperature sufficiently high to allow the organ to be perfused at an arterial perfusate temperature equal to or above the target temperature.

25. The method of claim 24, further comprising storing the organ between cooling the organ to a temperature below the target temperature while perfusion of the organ remains interrupted and rewarming the organ.

26. The method as in dams 24 or 25, further comprising, after said rewarming to a temperature sufficiently high to allow the organ to be perfused at an arterial perfusate temperature equal to or above the target temperature:
  reperfusing the organ with the second cryoprotectant solution at perfusate temperature equal to or above the target temperature, and then
  replacing the second cryoprotectant solution with the first cryoprotectant solution;
  wherein the replacement of the second cryoprotectant solution with the first cryoprotectant solution lowers the arterial perfusate cryoprotectant concentration by 0.5-1.5 molar while the temperature is raised from below −20° C. to above −10° C.

27. The method of claim 26 wherein the warming rate from below −20° C. to above −10° C. is greater than 0.5° C./min and the rate of change of concentration during warming from below −20° C. to above −10° C. is between 50 miII/min and 1000 mM/min.

28. The method of claim 27 wherein the warming rate from below −20° C. to above −10° C. is between 2° C./min and 20° C./min.

29. The method of claim 26 wherein the arterial perfusion pressure is lowered at the time of, during, or following replacing the second cryoprotectant solution with the first cryoprotectant solution.

30. The method of claim 26 wherein the majority of the reduction in the arterial perfusate cryoprotectant concentration takes place above −10° C.

31. The method of claim 30 wherein the majority of the reduction in the arterial perfusate cryoprotectant concentration takes place above −5° C.

32. The method of claim 15 wherein the arterial perfusion pressure is 40±8 mmHg before perfusion with said first or second cryoprotectant solution.

33. The method of claim 32 wherein the arterial perfusion pressure is raised to 41-110 mmHg when perfusion with said first or second cryoprotectant solution begins.

34. The method of claim 15, further comprising, following completion of all steps of claim 15:
  replacing the second cryoprotectant solution with the first cryoprotectant solution while warming said organ from below −10° C. to a desired high temperature of −10° C. or above by continuous vascular perfusion with minimal injury, said warming comprising raising the temperature of the perfusate to or above a desired high temperature; and
  continuing to perfuse the organ without changing arterial concentration until the organ temperature is considered to reach said desired high temperature.

35. The method of claim 34, further comprising, following completion of all steps of claim 34:
  continuing to perfuse the organ at the desired high temperature for a time sufficiently long to protect the organ from injury resulting from subsequent perfusate dilution but not so long as to cause undesired injury from continued exposure to the undiluted cryoprotectant at the desired high temperature; and diluting the cryoprotectant.

36. The method of claim 15, wherein the second cryoprotectant solution has a higher concentration than the first cryoprotectant solution.

37. The method of claim 15, further comprising, following completion of all steps of claim 15, the additional steps of:
  discontinuing perfusion of the organ with the second cryoprotectant solution;
  setting the temperature of the second cryoprotectant solution arterial perfusate to a desired high temperature >−10° C. while the organ remains unperfused by the arterial perfusate;
  resuming perfusion of the organ with said second cryoprotectant solution at said desired high temperature of −10° C. or above for a desired time; and
  diluting the second cryoprotectant solution.

38. The method of claim 37 wherein said desired time is 1-10 minutes.

39. The method of claim 37 wherein said dilution of the second cryoprotectant solution is made using a lower concentration of cryoprotectant that is itself vitrifiable at a cooling rate of ≤20° C./min.

40. The method of claim 39 wherein the lower concentration of cryoprotectant that is itself vitrifiable contains no added osmotic buffering agents.

41. The method of claim 39 wherein the lower concentration of cryoprotectant that is itself vitrifiable is devoid of the most toxic cryoprotectants present in the cryoprotectant that has been diluted by the lower concentration of cryoprotectant.

42. The method of claim 15, further comprising, following completion of all steps of claim 6, the additional steps of:
  warming the organ externally from below −10° C. to a desired high temperature of −10° C. or above; and
  perfusing the organ at an arterial temperature equal to or above said desired high temperature of >−10° C. with a reduced concentration of cryoprotectant that does not contain a non-penetrating osmotic buffering agent.

* * * * *

UNITED STATES PATENT AND TRADEMARK OFFICE
CERTIFICATE OF CORRECTION

| | | |
|---|---|---|
| PATENT NO. | : 8,679,735 B2 | Page 1 of 1 |
| APPLICATION NO. | : 10/571968 | |
| DATED | : March 25, 2014 | |
| INVENTOR(S) | : Gregory M. Fahy et al. | |

It is certified that error appears in the above-identified patent and that said Letters Patent is hereby corrected as shown below:

In the Claims:

In claim 26, column 27, line 14, "dams 24 or 25," should read --claims 24 or 25,--.

In claim 26, column 27, line 19, "at perfusate temperature" should read --at an arterial perfusate temperature--.

In claim 27, column 27, line 31, "50 mill/min" should read --50 mM/min--.

Signed and Sealed this
Seventeenth Day of June, 2014

Michelle K. Lee
*Deputy Director of the United States Patent and Trademark Office*